US009814490B2

United States Patent
Neoh et al.

(10) Patent No.: US 9,814,490 B2
(45) Date of Patent: Nov. 14, 2017

(54) DEFLECTABLE ACCESS SHEATH HANDLE WITH LOCKING MECHANISM

(71) Applicant: Cook Medical Technologies LLC, Bloomington, IN (US)

(72) Inventors: WenHong Neoh, Bloomington, IN (US); Robert M. Eells, Bloomington, IN (US); Jeffrey S. Melsheimer, Springville, IN (US); Kristen Michelle Van Wyk, Bloomington, IN (US); Tyler J. Bunch, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 443 days.

(21) Appl. No.: 14/520,448

(22) Filed: Oct. 22, 2014

(65) Prior Publication Data

US 2015/0119800 A1    Apr. 30, 2015

Related U.S. Application Data

(60) Provisional application No. 61/895,566, filed on Oct. 25, 2013.

(51) Int. Cl.
*A61B 17/34* (2006.01)
*A61B 1/00* (2006.01)
(Continued)

(52) U.S. Cl.
CPC ........ *A61B 17/3468* (2013.01); *A61B 1/0052* (2013.01); *A61B 1/00135* (2013.01);
(Continued)

(58) Field of Classification Search
CPC .......... A61B 17/3468; A61B 2017/347; A61B 2017/00318; A61B 2017/00327;
(Continued)

(56) References Cited

U.S. PATENT DOCUMENTS 6,530,897 B2    3/2003  Nardeo
6,572,610 B2    6/2003  Kovalcheck et al.
(Continued)

FOREIGN PATENT DOCUMENTS

EP     1 803 481 A2    4/2007
EP     1 803 481 A3    5/2007
(Continued)

OTHER PUBLICATIONS

Extened European Search Report for Application No. 14189784.3-1660, 6 pp., dated Feb. 25, 2015.

*Primary Examiner* — Kami A Bosworth
*Assistant Examiner* — Alexandra Lalonde
(74) *Attorney, Agent, or Firm* — Brinks Gilson & Lione

(57) ABSTRACT

An elongate access sheath comprises a proximal portion and a lumen. The proximal portion supports a control handle, a brake pad, a tension gear, and a locking trigger. A deflector filament extends through the lumen and is coupled to the tension gear. The tension gear includes an outside and an inner engagement portion. The brake pad comprises a slot and an outside engagement portion. The locking trigger includes a pin disposed within the brake pad slot. The control handle includes a lever and an engagement portion. Upward movement of the lever engages the engagement portion with the outside engagement portion of the tension gear to rotate the tension gear in a first direction and slides the deflector filament to bend the lumen distal portion. Translation of the locking trigger engages the brake pad and the tension gear to prevent rotation of the tension gear in an opposite second direction.

14 Claims, 19 Drawing Sheets

(51) Int. Cl.
*A61B 1/005* (2006.01)
*A61M 25/01* (2006.01)
*A61B 17/00* (2006.01)

(52) U.S. Cl.
CPC .... *A61M 25/0136* (2013.01); *A61M 25/0147* (2013.01); *A61B 2017/00318* (2013.01); *A61B 2017/00327* (2013.01); *A61B 2017/00407* (2013.01); *A61B 2017/00464* (2013.01); *A61B 2017/00469* (2013.01); *A61B 2017/00778* (2013.01); *A61M 2025/015* (2013.01)

(58) Field of Classification Search
CPC .......... A61B 2017/00464; A61B 2017/00323; A61M 2025/015; A61M 25/0136; A61M 25/0133; A61M 25/0147
See application file for complete search history.

(56) References Cited

U.S. PATENT DOCUMENTS

| | | | |
|---|---|---|---|
| 6,652,506 B2 | 11/2003 | Bowe et al. | |
| 7,497,853 B2 | 3/2009 | Fischer et al. | |
| 8,096,985 B2 | 1/2012 | Legaspi et al. | |
| 8,444,626 B2 | 5/2013 | Fischer et al. | |
| 2007/0156116 A1 | 7/2007 | Gonzalez | |
| 2010/0004606 A1* | 1/2010 | Hansen | A61F 2/95 604/264 |
| 2010/0312055 A1* | 12/2010 | Konstorum | A61B 1/00066 600/131 |
| 2011/0088498 A1* | 4/2011 | Ettwein | A61B 1/00075 74/479.01 |
| 2012/0277730 A1 | 11/2012 | Salahieh et al. | |
| 2013/0204096 A1* | 8/2013 | Ku | A61B 1/00066 600/301 |
| 2014/0088497 A1* | 3/2014 | Campbell | A61M 25/0136 604/95.04 |

FOREIGN PATENT DOCUMENTS

| | | |
|---|---|---|
| WO | WO 2009/007432 A1 | 1/2009 |
| WO | WO 2010/113072 A2 | 7/2010 |
| WO | WO 2010/113072 A3 | 7/2010 |

\* cited by examiner

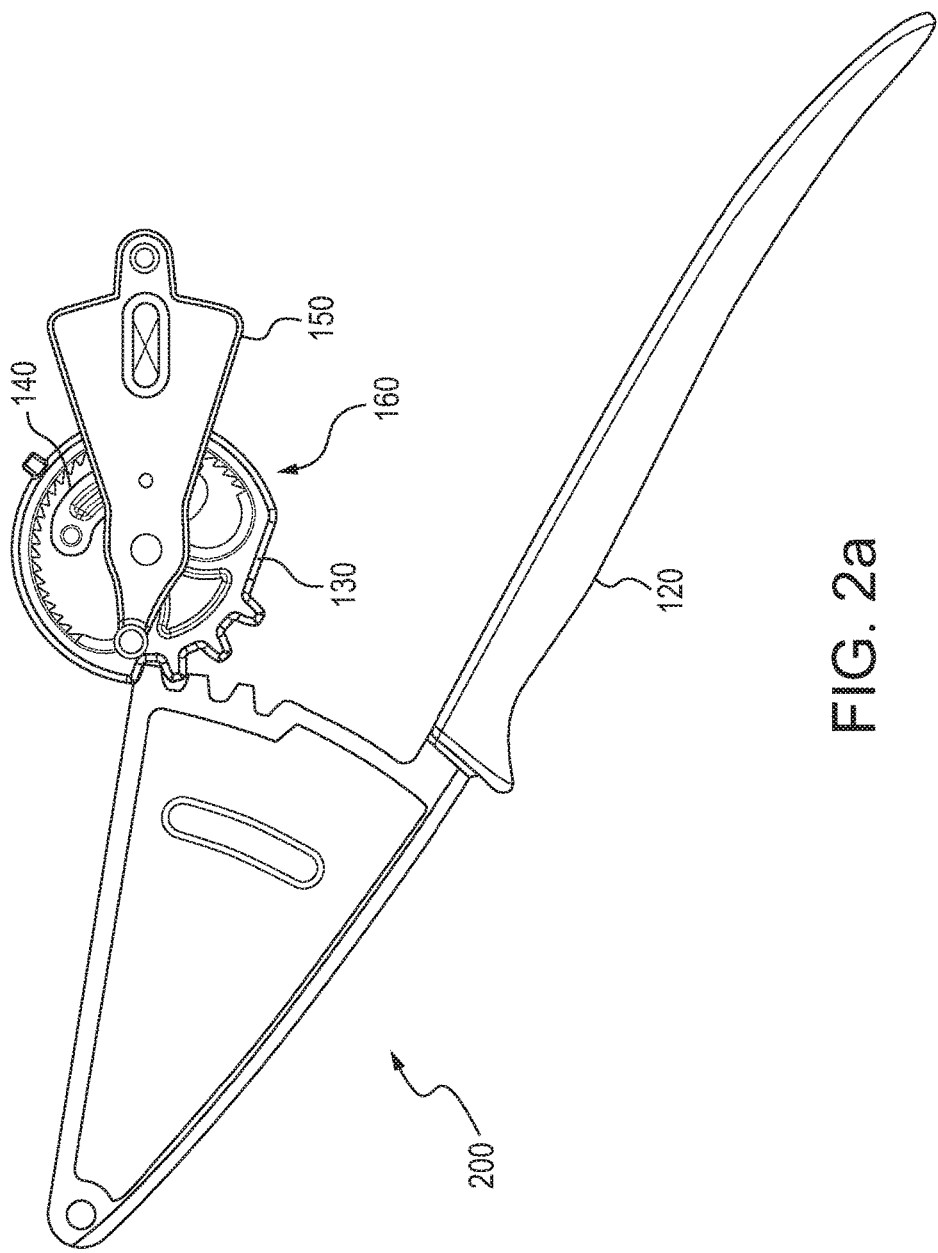

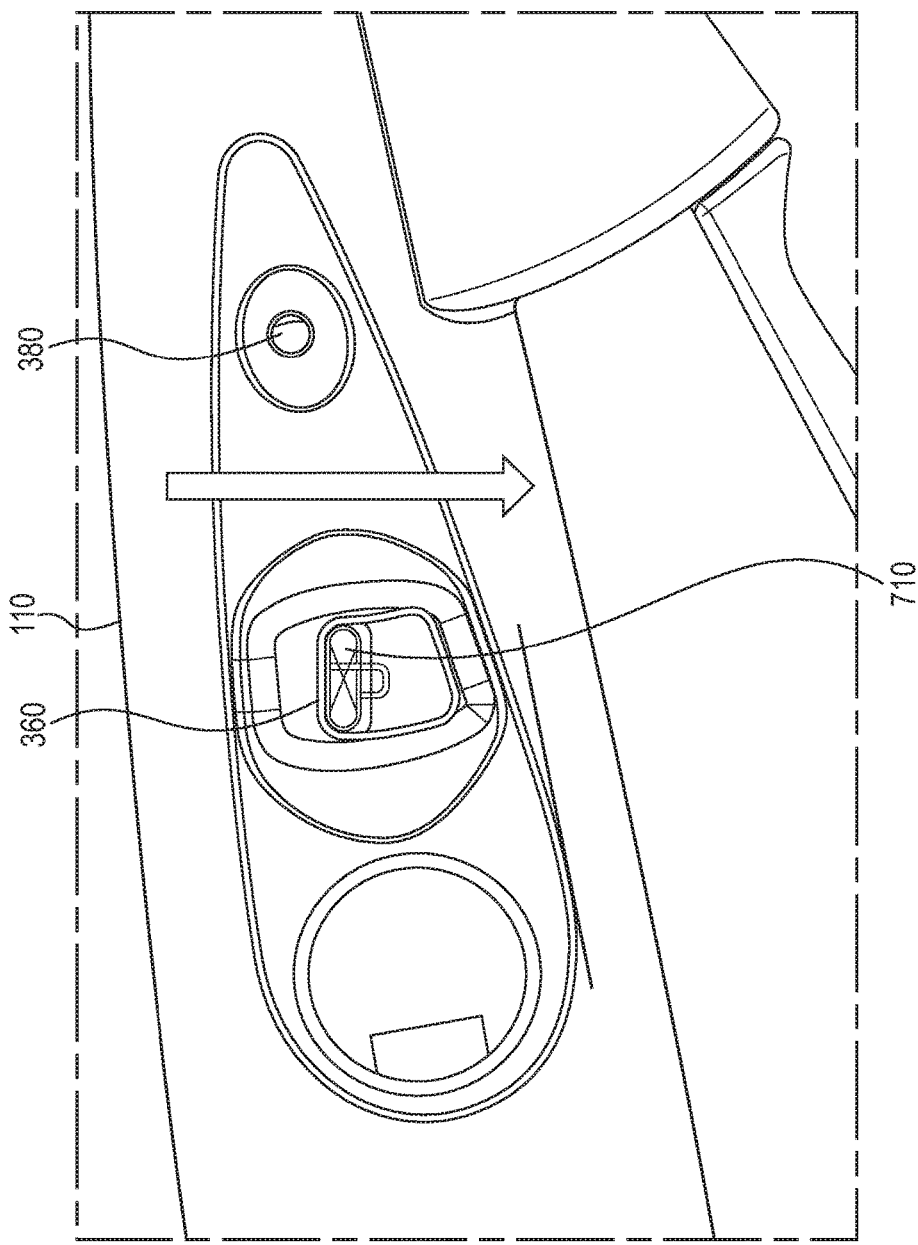

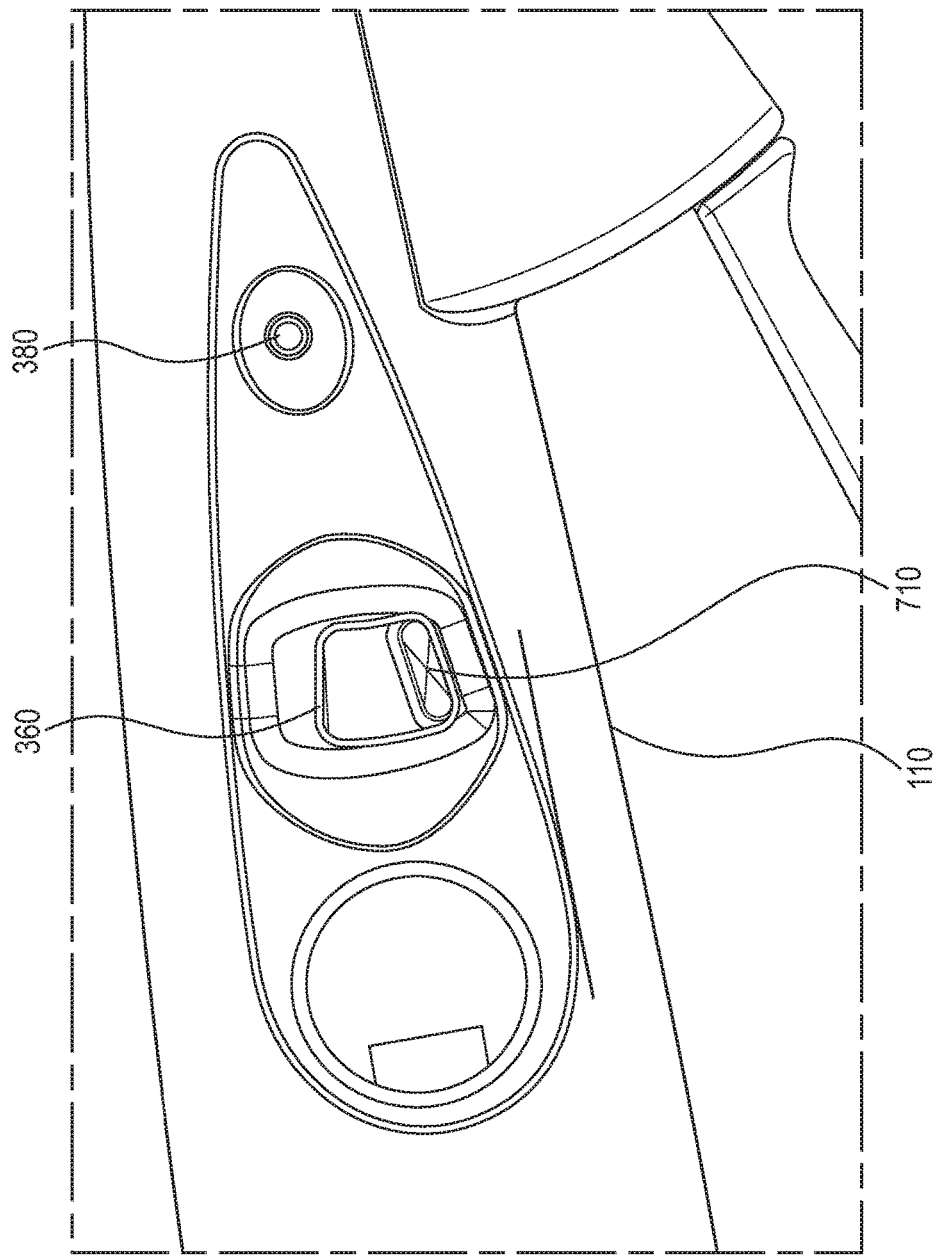

DEFLECTABLE ACCESS SHEATH HANDLE WITH LOCKING MECHANISM

CROSS-REFERENCE TO RELATED APPLICATIONS

This application claims priority from U.S. provisional application No. 61/895,566, filed on Oct. 25, 2013, the entirety of which is hereby fully incorporated by reference herein.

TECHNICAL FIELD

This disclosure relates to devices for the manipulation and guidance of medical tools within the body, in particular medical devices with a deflectable distal end.

BRIEF SUMMARY

An elongate access sheath comprises a distal portion, a proximal portion, and a lumen. The proximal portion supports a control handle, a brake pad, a tension gear, and a locking trigger. A deflector filament extends through the lumen and is coupled to the tension gear. The tension gear is rotatably mounted to the proximal portion and includes an outside engagement portion and an inner engagement portion. The brake pad is disposed within the hollow center of the tension gear and comprises a slot and an outside engagement portion. The locking trigger is attached to the tension gear and includes a pin that is disposed within the slot of the brake pad. The control handle includes a lever and an engagement portion. Upward movement of the lever causes the engagement portion to mesh with the outside engagement portion of the tension gear to rotate the tension gear in a first direction and slides the deflector filament within the lumen to bend the distal end. Translation of the locking trigger engages the brake pad and the tension gear to prevent rotation of the tension gear in an opposite second direction.

In one embodiment, an elongate access sheath comprises a distal portion, a proximal portion, and an elongate portion extending therebetween, the elongate portion defines a lumen therethrough, and the distal portion is bendable with respect to a longitudinal axis of the elongate portion. The proximal portion supports a control handle, a brake pad, and a tension gear. The deflector filament slidably extends through the lumen and is operatively coupled to the distal portion and the tension gear, wherein the at least one deflector filament is mounted so that rotation of the tension gear urges sliding movement within the lumen. The tension gear is rotatably mounted to the proximal portion and includes an outside engagement portion, wherein the outside engagement portion has teeth that are located on an outside engagement portion of the tension gear. The control handle comprises a lever portion and an engagement portion that comprises input teeth. The input teeth of the engagement portion are meshed with the outside engagement portion of the tension gear such that upward movement of the lever portion causes rotation of the tension gear in a first direction and sliding motion of the deflector filament within the lumen urges the distal portion to bend with respect to the longitudinal axis.

In another embodiment, an elongate access sheath comprises a distal portion, a proximal portion, and an elongate portion extending therebetween, the elongate portion defines a lumen therethrough, and the distal portion is bendable with respect to a longitudinal axis of the elongate portion. The proximal portion supports a control handle, a brake pad, a tension gear, and a locking trigger. The deflector filament slidably extends through the lumen and is operatively coupled to the distal portion and the tension gear, wherein the at least one deflector filament is mounted so that rotation of said tension gear urges sliding movement within said lumen. The tension gear is rotatably mounted to the proximal portion and includes an outside engagement portion and an inner engagement portion, wherein the outside engagement portion comprises teeth that are located on an outside engagement portion of the tension gear, and the inner engagement portion comprises teeth that are located upon a surface of a hollow center of said tension gear. The brake pad is disposed within said hollow center of said tension gear and comprises a slot and an outside engagement portion, wherein said opening is disposed vertically on said brake pad and an outside engagement portion is located on the outside engagement portion of the brake pad and aligned to engage the inner engagement portion of the tension gear. The locking trigger is attached to the tension gear and includes a body portion and a pin, wherein the pin is disposed within the slot of the brake pad. The control handle comprises a lever portion and an engagement portion that comprises input teeth, wherein the input teeth of the engagement portion are meshed with the outside engagement portion of said tension gear such that upward movement of the lever portion causes rotation of the tension gear in a first direction and sliding motion of the deflector filament within the lumen to urge the distal portion to bend with respect to the longitudinal axis, wherein translation of the locking trigger causes the pin to slide within the slot and urge engagement between the brake pad and the tension gear thereby preventing rotation of the tension gear in an opposite second direction, wherein the outside engagement portion prevents the rotation of the tension gear in an opposite second direction.

In another embodiment, an elongate access sheath provides for an engagement between said brake pad and said tension gear to form a ratchet. The ratchet is formed from the outside engagement portion of the brake pad that is comprised of angled teeth and the outside engagement portion of the tension gear that is comprised of angled teeth, wherein the angled teeth are angled in an opposite second direction to restrict movement of the tension gear when the brake pad and the tension gear are engaged. The ratchet formed allows further rotation of the tension gear in a first direction upon additional upward movement of the lever portion while preventing rotation of the tension gear in an opposite second direction.

In another embodiment, an elongate access sheath comprises a distal portion, a proximal portion, and an elongate portion extending therebetween, the elongate portion defines a lumen therethrough, and the distal portion is bendable with respect to a longitudinal axis of the elongate portion. The proximal portion supports a control handle, a brake pad, a tension gear, and a locking trigger. The deflector filament slidably extends through the lumen and is operatively coupled to the distal portion and the tension gear, wherein the at least one deflector filament is mounted such that rotation of said tension gear urges sliding movement within the lumen. The tension gear is rotatably mounted to the proximal portion and includes an outside engagement portion and an inner engagement portion, wherein the outside engagement portion comprises teeth that are located on an outside engagement portion of the tension gear. The brake pad is disposed within the hollow center of the tension gear and comprises a slot and a friction portion, wherein the opening is disposed vertically on the brake pad and the friction portion is located on the outside engagement portion of the brake pad and aligned to engage the inner engagement portion of the tension gear. The locking trigger is attached to the tension gear and includes a body portion and a pin, wherein the pin is disposed within the slot of said brake pad. The control handle comprises a lever portion and an engagement portion that comprises input teeth, wherein the input teeth of the engagement portion are meshed with the outside engagement portion of the tension gear such that upward movement of the lever portion causes rotation of the tension gear in a first direction and sliding motion of the deflector filament within the lumen to urge the distal portion to bend with respect to the longitudinal axis, wherein translation of the locking trigger causes the pin to slide within the slot and urge engagement between the brake pad and the tension gear thereby preventing rotation of the tension gear in an opposite second direction.

In another embodiment, a method of deflecting the distal end of a lumen of an elongate access sheath which includes a control handle, a tension gear, and a deflector filament attached proximally to the tension gear and distally to the lumen. The method includes the steps of actuating the control handle in an upward direction, wherein the actuating causes the control handle to engaged the tension gear and to cause rotation of the tension gear in a first direction. Further, sliding the filament in a proximal direction to urge the distal end to bend with respect to the longitudinal axis.

In another embodiment, a method of deflecting the distal end of a lumen of an elongate access sheath that further includes a brake pad and a locking trigger. The method further includes the steps of translating the locking trigger to bring the brake pad in contact with the locking trigger. Further, the locking trigger is prevented from moving in a second direction which prevents the deflector filament from returning to a configuration along the longitudinal axis.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The accompanying drawings are included to provide a further understanding of the claims, are incorporated in, and constitute a part of this specification. The detailed description and illustrated examples described serve to explain the principles defined by the claims.

FIG. 1b is a cross-sectional side view of the deflecting mechanism of the deflectable access sheath of FIG. 1a.

FIG. 2a is a cross-sectional view of the deflecting mechanism of the deflectable access sheath of FIGS. 1a-1b.

FIG. 11a shows a partial side view of the deflectable access sheath before the locking trigger is actuated by the user.

FIG. 11b shows a partial side view of the deflectable access sheath after the locking trigger is actuated by the user.

DETAILED DESCRIPTION OF THE INVENTION

Figure 1A:
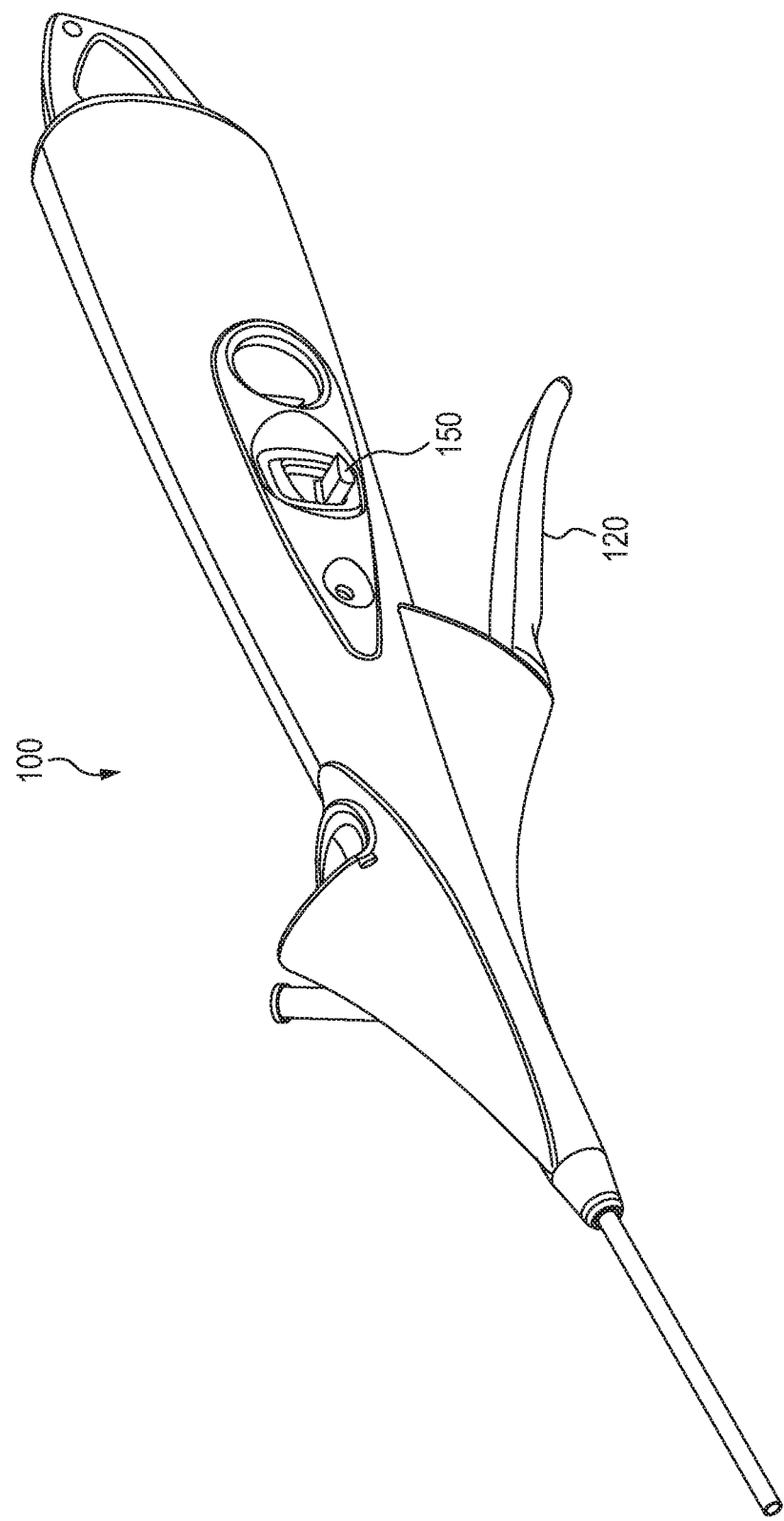
FIG. 1a is a perspective view of an embodiment of the deflectable access sheath.

The embodiments described in this disclosure will be discussed generally in relation to the use of deflectable sheaths in the manipulation and guidance of operating and imaging tools in urological procedures such as lithotripsy, but the disclosure is not so limited and may be applied to the use of other deflectable medical devices in procedures in other vasculature or other body vessels or lumens.

In the present application, the term "proximal" refers to a direction that is generally closest to the operator of the device during a medical procedure, while the term "distal" refers to a direction that is furthest from the operator of the device.

The present deflectable access sheath operates to allow the controlled deflection of the distal end of the deflectable access sheath away from a linear conformation. In particular, the deflectable access sheath may provide for a locking mechanism that locks the angle of the deflectable end of the deflectable access sheath. This locking mechanism allows for better control and use of the device during the procedure and allows the user to perform various other procedures during the ureteroscopy. The locking mechanism can be released to allow for the increased deflection of the deflectable end or for the deflectable end to return to a linear conformation.

The deflectable access sheath may further allow the deflection of the deflectable end while the deflectable access sheath is in a locked position. In one example, a ratcheting mechanism allows the incremental deflection of the deflectable end. Each incremental deflection is locked into place by the locking mechanism. This ratchet aspect allows the user on-the-spot modification of the deflection angle of the deflectable end.

Once the desired angle of the distal end of the deflectable access sheath is achieved, accessories and/or other medical devices, such as laser fibers, optical fibers, wire guides, stone-breakers, and/or stone removal tools, can be inserted through the working channel and used for that particular procedure.

The present device provides a handle design that allows the user to access the sheath closer to hip-level which allows the user to transfer more torque to twist the device and grip power to actuate the device. This results in less fatigue of the user. The handle design of the present device is more fully described with reference to U.S. application Ser. No. 29/461,908 (filed Jul. 29, 2013) and commonly assigned to the assignee of this application, which is hereby incorporated by reference in its entirety.

As described more fully below with regard to FIGS. 1-3, the sheath handle assembly 100 has a control handle 120 that accomplishes the above functions. The sheath handle assembly 100 is composed of four main parts—a sheath housing 110, a control handle 120, a locking trigger 150 and a gear locking system 160 that is composed of a tension gear 130 and a brake pad 140.

In operation, the sheath housing 110 is held by the user and the control handle 120 is compressed in an upward direction. This upward compression translates into a clockwise rotational movement of the tension gear 130. The movement of the tension gear 130 translates into the longitudinal movement of the tension wire 170 which causes deflection of the distal end of the sheath handle assembly 100 (not pictured here). The locking trigger 150 is actuated by a downward movement that engages the gear locking system 160. This engagement brings the outer teeth of the brake pad 140 in contact with the inner teeth of the tension gear 130. Subsequent compression of the control handle 120 results in the incremental movement of the tension wire 170 as defined by the inner teeth of the tension gear 130. This provides for incremental adjustment of the deflection of the distal end of the sheath handle assembly 100 (not pictured here), while preventing the return of the distal end to a linear configuration.

Figure 2B:
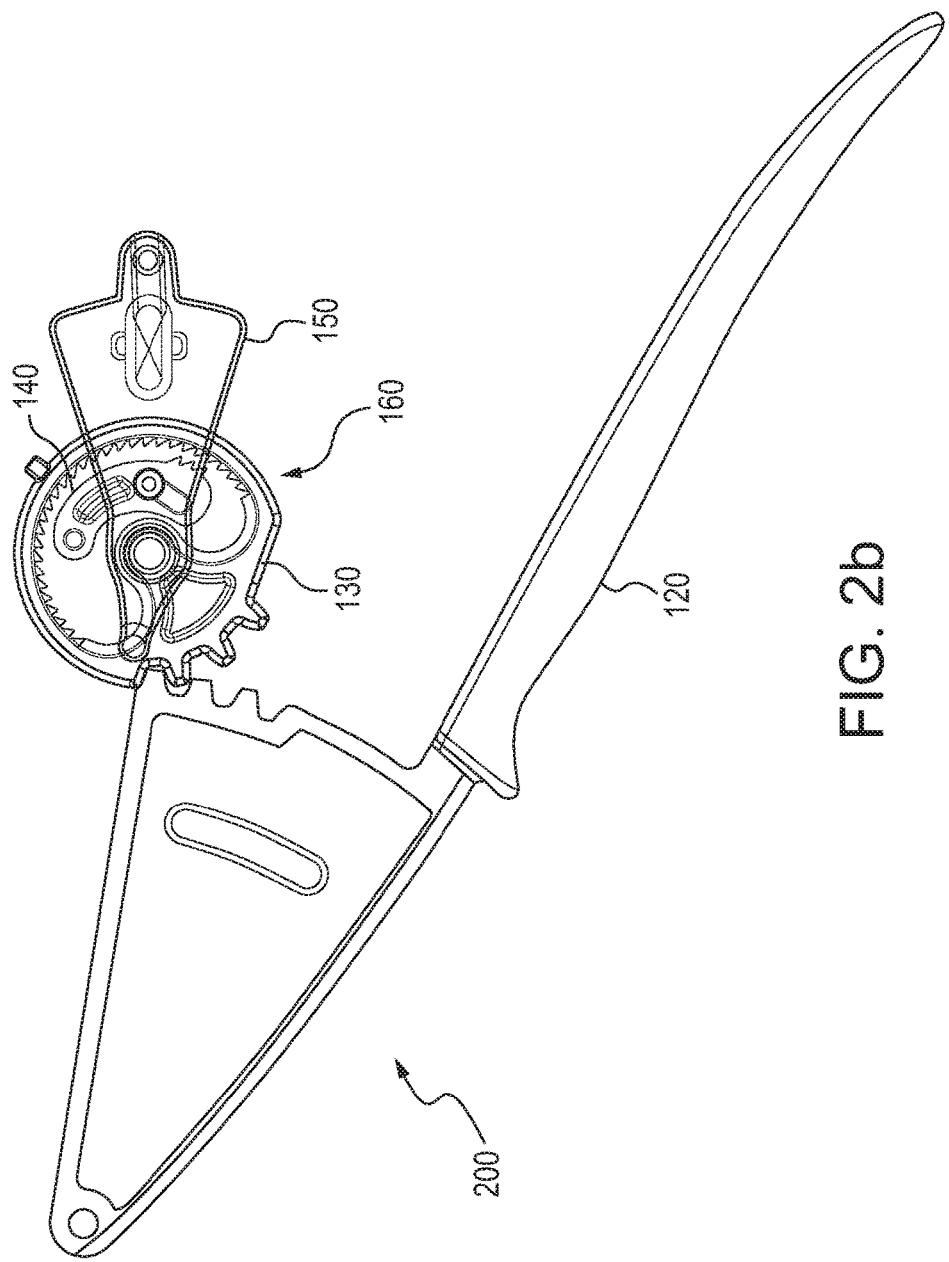
FIG. 2b is a cross-sectional view of the deflecting mechanism of the deflectable access sheath of FIG. 2a where the locking trigger is shown transparent to better see the connections of the gear locking system.
Figure 3:
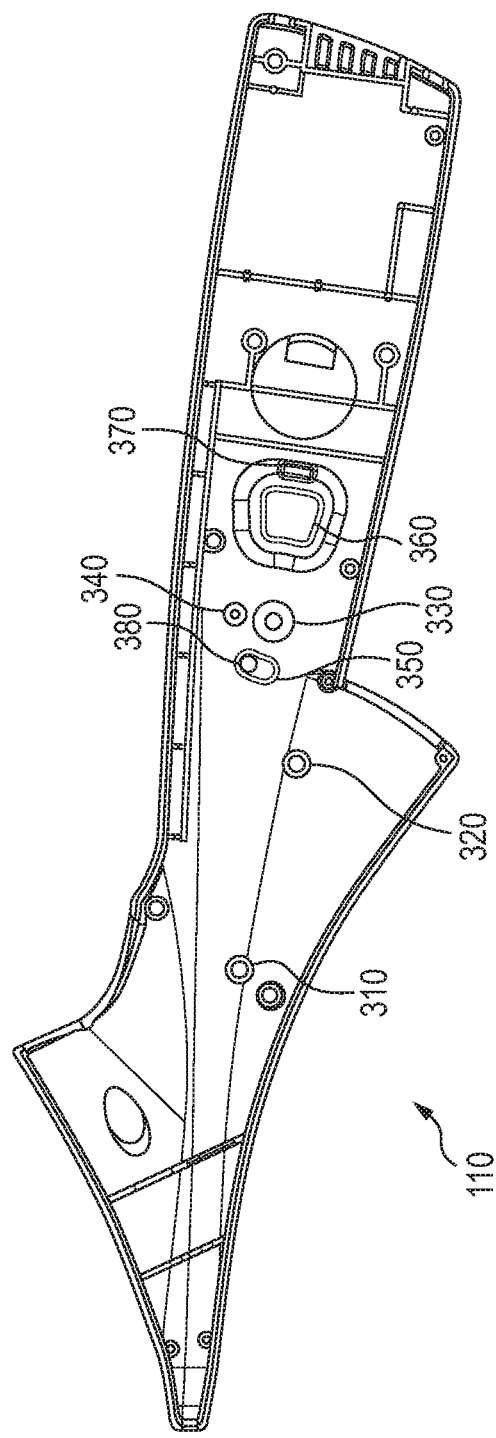
FIG. 3 is a cross-sectional side view of the sheath housing of a deflectable access sheath.
Figure 12A:
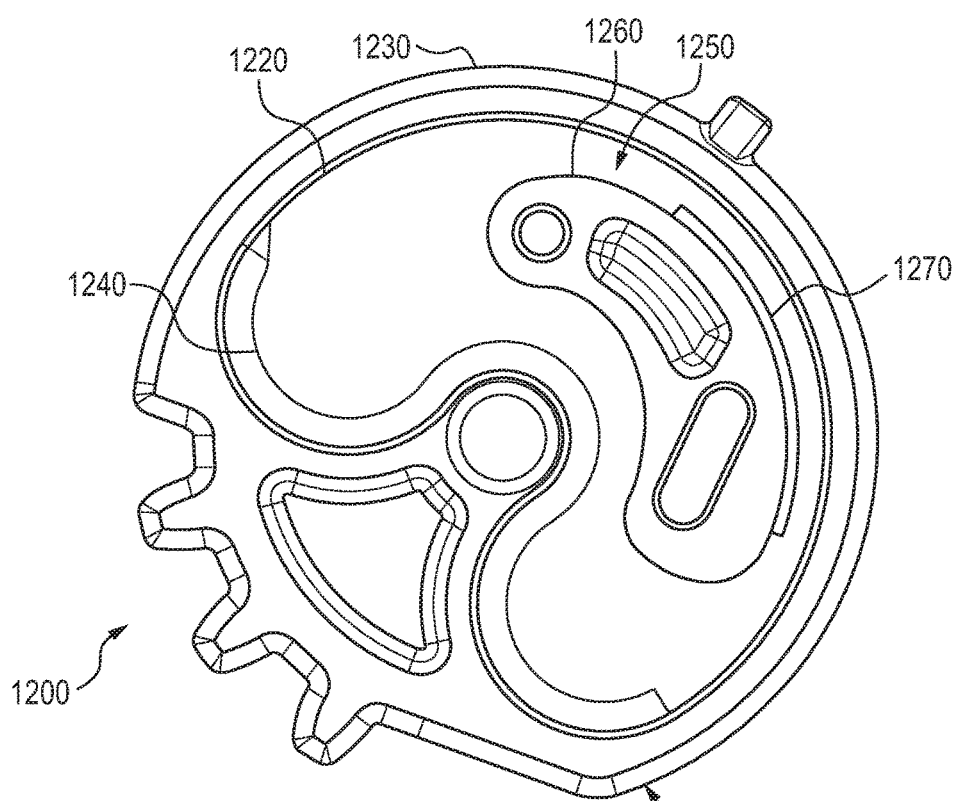
FIG. 12a shows a side view of an alternative embodiment of the deflecting mechanism.
Figure 12B:
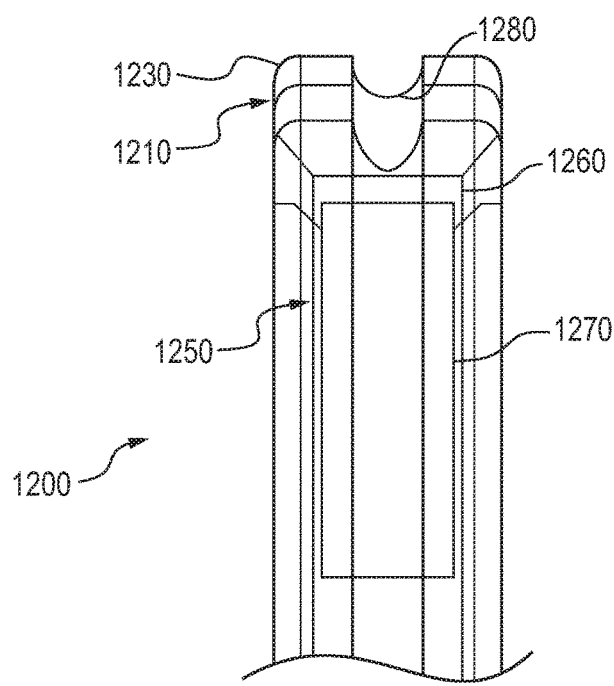
FIG. 12b shows a transparent alternate side view of an alternative embodiment of the deflecting mechanism.

FIGS. 1-3 illustrate an embodiment of the sheath handle assembly 100. FIGS. 4-7 illustrate components of an embodiment of the sheath handle assembly 100. FIGS. 8a-b illustrate the sheath handle assembly 100 as it is operated by a user to deflect the distal end of the sheath handle assembly 100. FIGS. 9-11 illustrate the sheath handle assembly 100 as the gear locking system 160 is actuated. FIGS. 12a-b illustrate an alternative embodiment of the gear locking system 160 of FIG. 1.

Figure 1B:
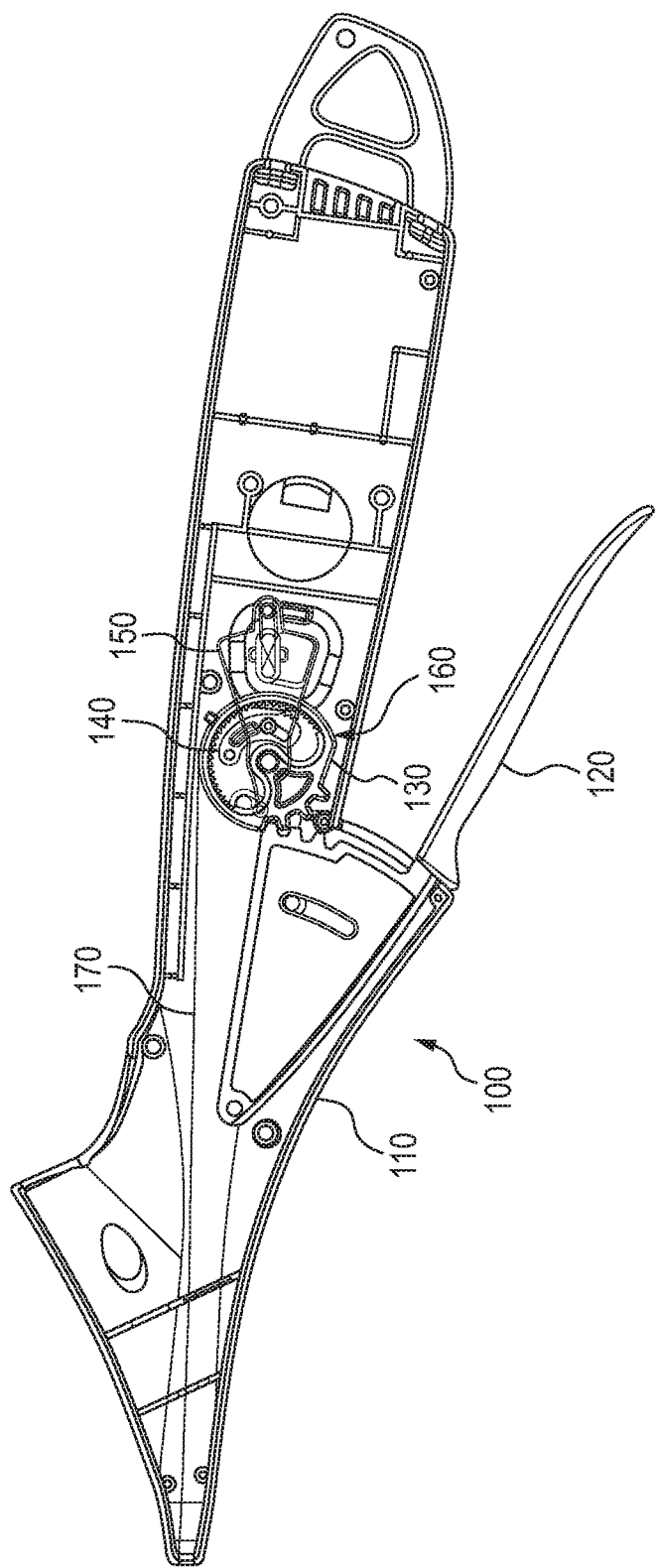

FIGS. 1a-b show the multiple components of the sheath handle assembly 100 as they are interconnected. FIG. 1a provides a proximal view of the sheath handle assembly 100 with sheath housing 110, control handle 120, and a portion of the locking trigger 150. Connected to the distal end of the sheath handle assembly 100 is a lumen with a deflectable end (not pictured here) that will be further discussed in FIGS. 8a-b. FIG. 1b shows a cross-sectional view of the sheath handle assembly 100 that includes a sheath housing 110, a control handle 120, a gear locking system 160 which is made up of the tension gear 130 and the brake pad 140, a locking trigger 150, and a tension wire 170. Each of the individual components of the sheath handle assembly 100 will be described in further detail below.

FIGS. 2a-b provide enlarged cross-sectional views of the locking mechanism 200 of the sheath handle assembly 100 and the interconnections of the various components of the sheath handle assembly 100. The locking mechanism 200 includes the control handle 120, the gear locking system 160 which is made up of the tension gear 130, the brake pad 140, and the locking trigger 150.

FIG. 3 provides a cross-sectional view of the sheath housing 110 with receptors built into the inside of the sheath housing 110 to provide for the containment and controlled movement of the various components in the sheath handle assembly 100 as described in FIGS. 1-2. The control handle 120 is rotatably connected to the sheath housing 110 through a pin that is inserted through the control handle 120 and fits into the handle slot 310. The pin connected through the handle slot 310 allows the control handle 120 rotational movement about the pin. The movement of the control handle 120 is further controlled by a pin that fits into handle movement slot 320 of the sheath housing 110, described in further detail below.

The locking trigger 150 and the tension gear 130 is rotatably connected to the sheath housing 110 by a pin that is connected through the slot 330 of the sheath housing 110. As will be described in further detail, the pin at slot 330 fits through the tension gear locking trigger 150 which is disposed about the tension gear 130.

The brake pad 140 is connected to the sheath housing 110 through a pin that is rotatably connected to the sheath housing 110 through a pin that is inserted through the brake pad 140 and fits into the brake slot 340 of the sheath housing 110. The pin connected through the brake slot 340 allows the brake slot 340 rotational movement about the pin. As will be discussed further, movement of the locking trigger 150 rotates the brake pad 140 to bring it in contact with tension gear 130.

The sheath housing 110 of FIG. 3 also provides for other connections that allows for the actuation of the locking trigger 150. The actuating braking slot 360 provides for the protrusion of the locking mechanism actuator (not pictured here) to protrude from the sheath housing 110 so that it is visible to the user. The distal end of the locking trigger 150 fits into the locking trigger indicator slot 350 which limits the extent of the movement of the distal end of the locking trigger 150. The locking trigger pin indicator 380 allows for the distal end of the locking trigger indicator slot 350 to be visible when the locking trigger 150 is actuated. The locking trigger 150 is prevented from moving by the locking trigger protrusion 370 which keeps the proximal end of the locking trigger 150 in either the non-actuated or actuated position.

FIGS. 4-7 illustrate the individual components of an embodiment of the sheath handle assembly 100.

Figure 4A:
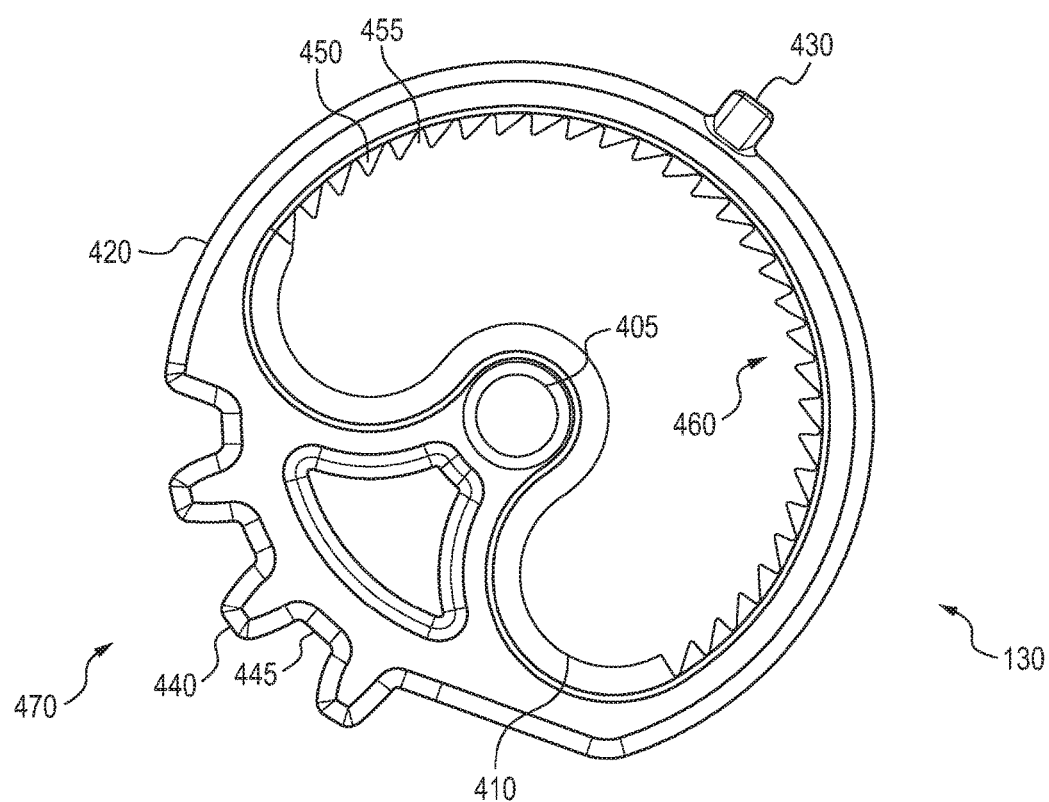
FIG. 4a illustrates a side view of the tension gear of the deflecting mechanism in FIGS. 2a-b.
Figure 4B:
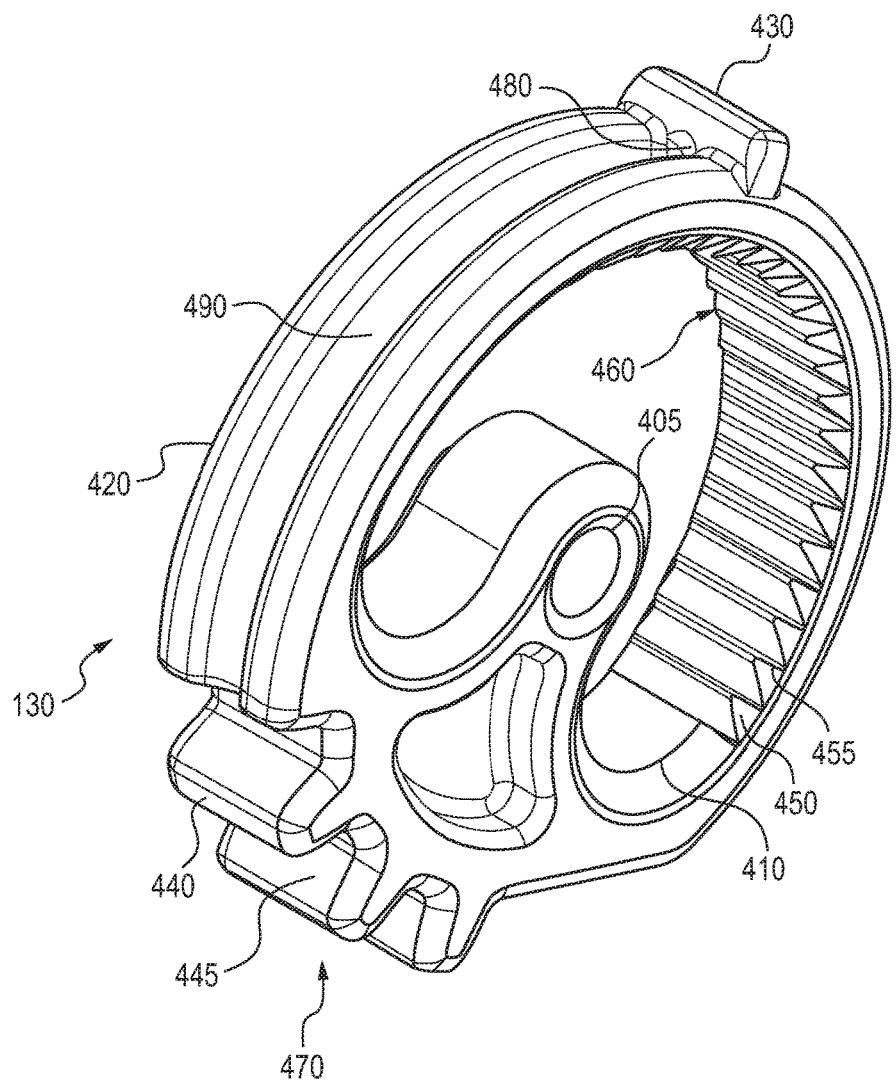
FIG. 4b illustrates a perspective view of the tension gear of the deflecting mechanism in FIGS. 2a-b.

FIGS. 4a-b provide a side and perspective view of the tension gear 130 of the gear locking system 160 of FIGS. 1b and 2a-b. In the present embodiment, the tension gear 130 has an outer surface 420 and an inner surface 410. The tension gear 130 is rotatably connected to the sheath housing 110 through the opening 405 which is disposed about a pin that is connected to slot 330 of FIG. 3.

The outer surface 420 includes an outer engagement portion 470 and a portion for engaging the tension wire 170 of FIG. 1 b. The outer engagement portion 470 is comprised of more than one tooth 440 and more than one tooth receiving end 445. This outer engagement portion 470 engages a series of teeth on a portion of the control handle 120 which cause the outer engagement portion 470 to rotate when the control handle 120 is actuated. The outer surface 420 also includes a filament anchor 430 which protrudes from the outer surface 420. The tension wire 170 of FIG. 1b is attached to the filament anchor 430 at the filament connection 480 and rests in the filament receptor 490. The filament receptor 490 is disposed between the filament anchor 430 and one end of the outer engagement portion 470. The length of the filament receptor 490 is at least equal to the length of the tension wire 170 needed to cause the maximum deflection of the lumen.

Figure 5A:
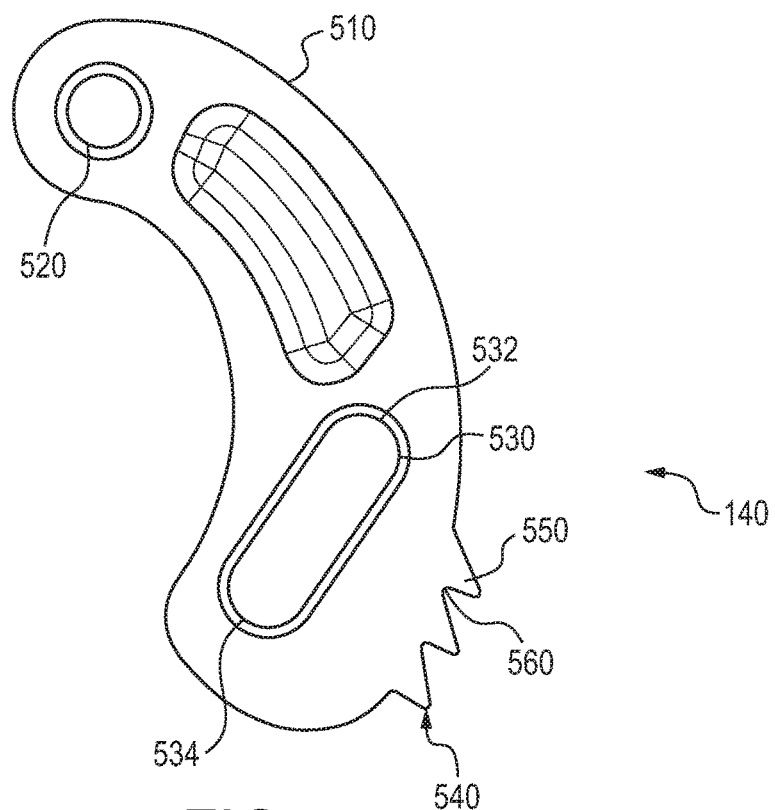
FIG. 5a illustrates a side view of the brake pad of the deflecting mechanism in FIGS. 2a-b.
Figure 5B:
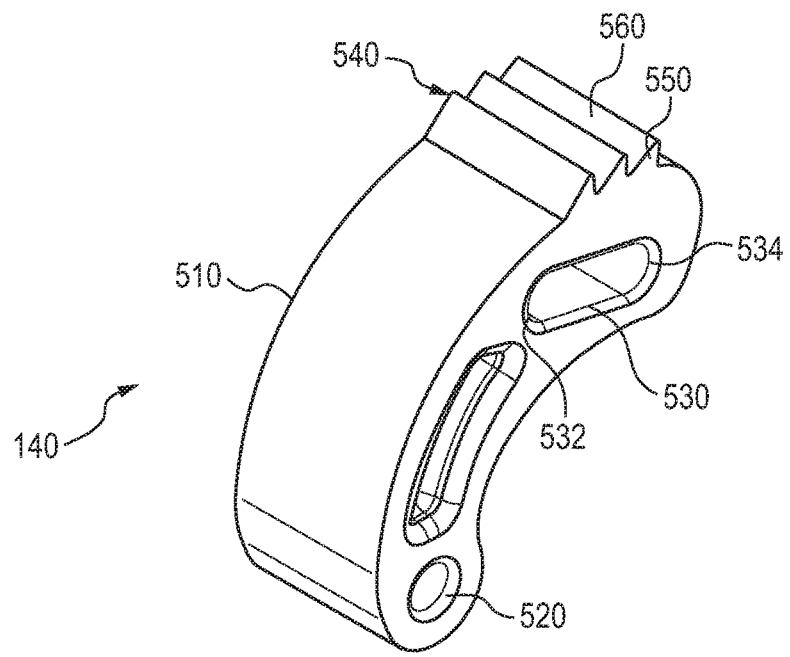
FIG. 5b illustrates a perspective view of the brake pad of the deflecting mechanism in FIGS. 2a-b.

The inner surface 410 has an inner engagement portion 460 that is composed of teeth to engage the teeth portion of the brake pad 140 shown in FIGS. 5a-b. The inner engagement portion 460 includes more than one sawtooth 450 and more than one sawtooth receiving end 455. As will be discussed below, when the inner engagement portion 460 is engaged, a ratcheting device is created. The shape of the sawtooth 450 and the sawtooth receiving end 455, provide for movement in a single direction and restricts movement in a counterclockwise direction at each sawtooth 450.

FIGS. 5a-b provide a side and perspective view of the brake pad 140 of the gear locking system 160 of FIGS. 1b and 2a-b. In the present embodiment, the brake pad 140 has an outer surface 510 and two points of connection to the sheath housing 110—an opening 520 and a slot portion 530 that define and restrict the movement of the brake pad 140.

The brake pad 140 is rotatably connected to the sheath housing 110 through the opening 520 which is disposed about a pin that can be fit into the brake slot 340. As will be further described below, the slot portion 530 is disposed about a pin that fits into the locking trigger 150. When the locking trigger 150 is actuated in either an upward or downward direction, the brake pad 140 is rotated a limited distance as defined by the slot portion 530.

The outer surface 510 of the brake pad 140 includes a ratchet portion 540 for engaging the inner engagement portion 460 of the tension gear 130. The ratchet portion 540 is comprised of more than one tooth 550 and more than one tooth receiving end 560. As described above, the shape of the tooth 550 and the tooth receiving end 560 act as a ratchet against the inner surface 410 of the brake pad 140. When the ratchet portion 540 of the brake pad 140 is brought into contact with the inner surface 410 of the tension gear 130, the tension gear 130 is allowed to move in a single direction, but the tooth 550 and the tooth receiving end 560 interact with the sawtooth 450 and sawtooth receiving end 455 of the tension gear 130 to prevent movement of the tension gear 130 in a counterclockwise direction at each sawtooth 450 and sawtooth receiving end 455 of the tension gear 130.

Figure 6A:
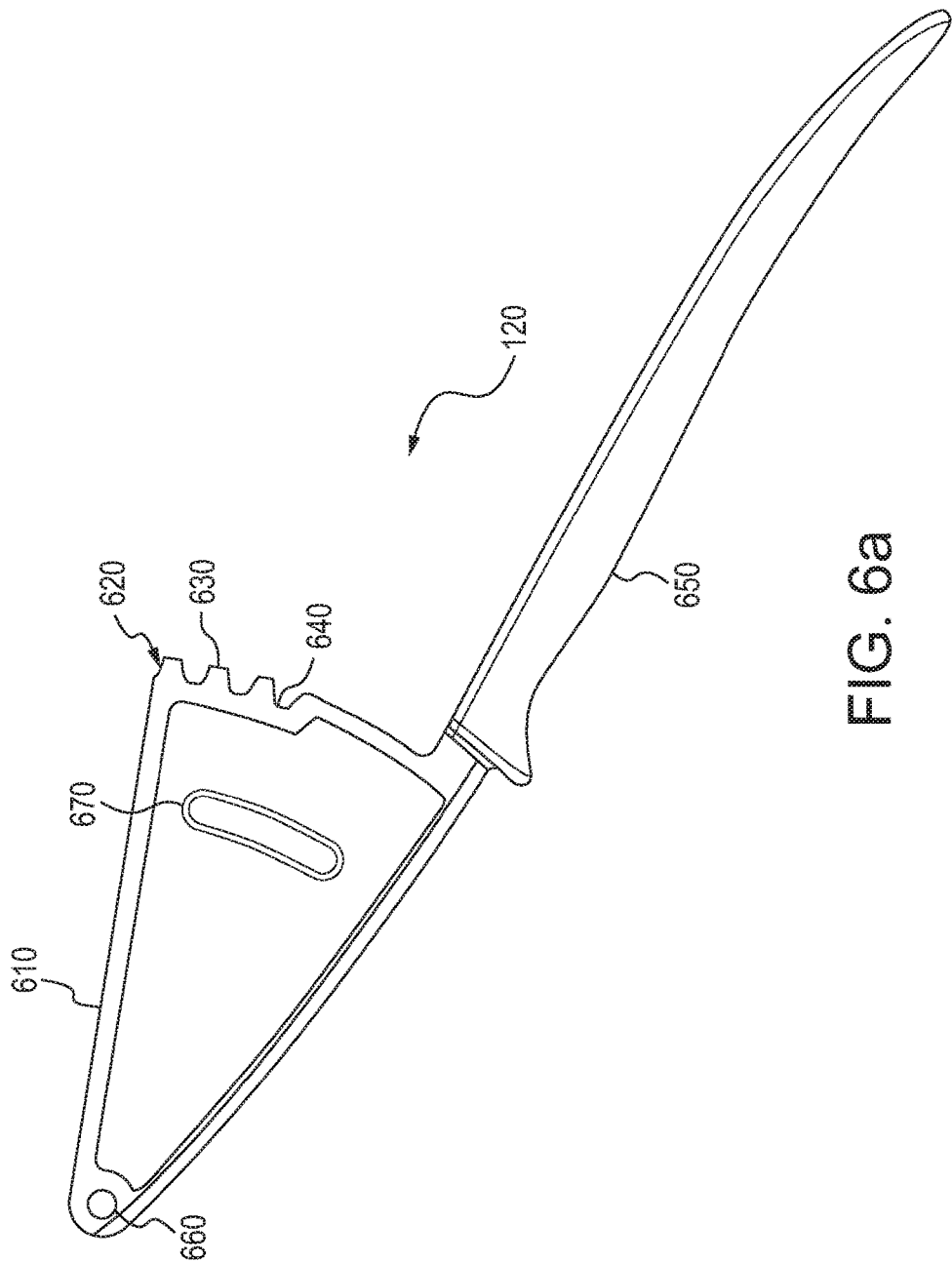
FIG. 6a illustrates a side view of the control handle of the deflecting mechanism in FIGS. 2a-b.
Figure 6B:
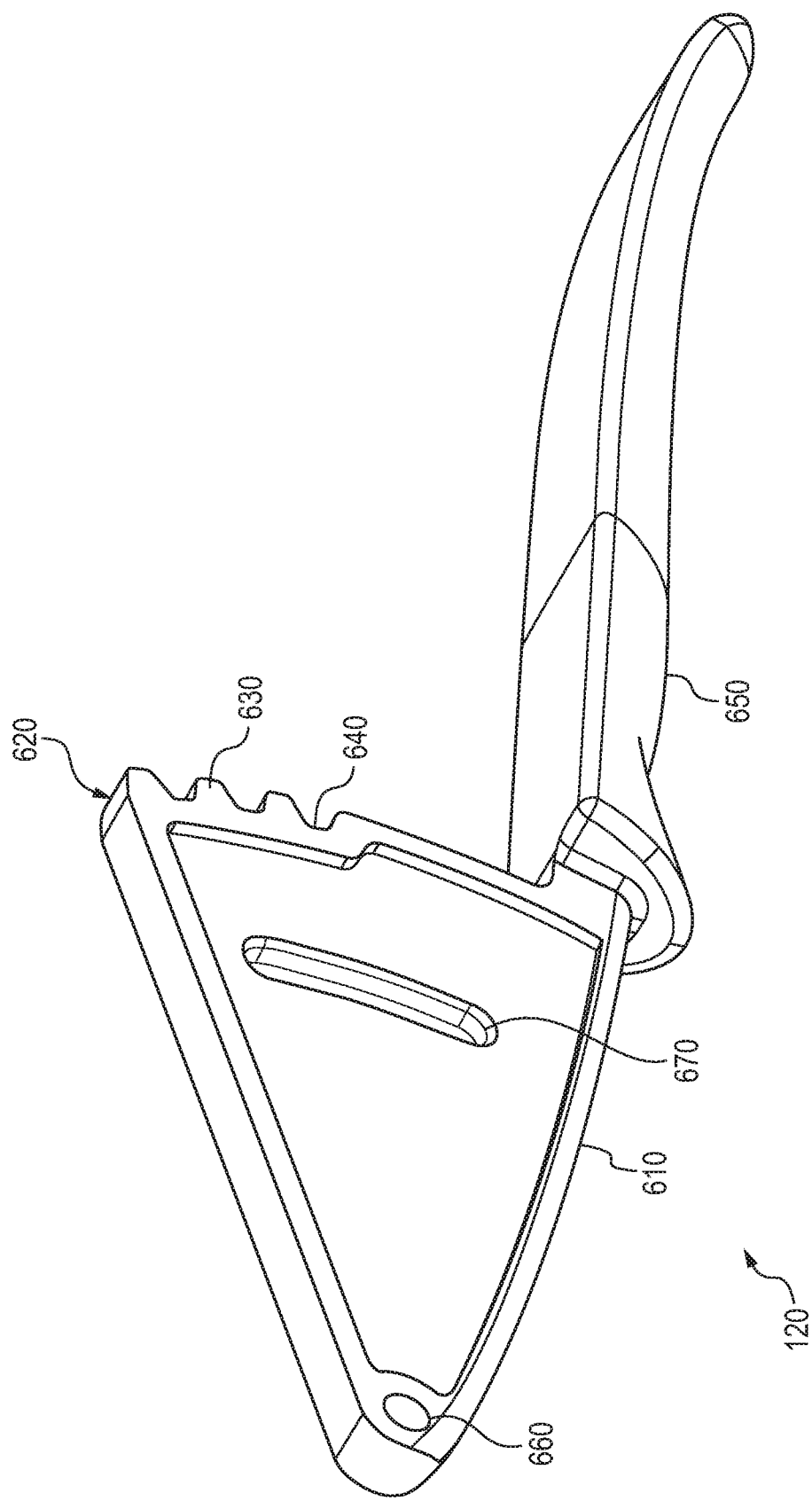
FIG. 6b illustrates a perspective view of the control handle of the deflecting mechanism in FIGS. 2a-b.

FIGS. 6a-b provide a side and perspective view of the control handle 120 of FIGS. 1b and 2a-b. In the present embodiment, the control handle 120 has a lever portion 650, an engagement portion 620 on the outer surface 610 and two points of connection to the sheath housing 110—an opening 660 and a slot portion 670 that define and restrict the movement of the control handle 120.

The control handle 120 is rotatably connected to the sheath housing 110 through the opening 660 which is disposed about a pin that can fit into the handle slot 310. The range of movement of the control handle 120 is limited by the slot portion 670. A pin fits into the handle movement slot 320 of the sheath housing 110 and the slot portion 670 is disposed about this pin. When the lever portion 650 of the control handle 120 is pulled in an upward direction, the rotational movement of the control handle 120 is limited by the length of the slot portion 670. Any or all embodiments of the lever portion 650 may be provided with gripping features that provide secure and/or ergonomic gripping of the handles by the user. Any or all of the handles may further be provided with a mechanism or ability to provide the user with tactile feedback while gripping and/or operating the handle.

The engagement portion 620 lies on the outer surface 610 of the control handle 120. Engagement portion 620 is composed of more than one input tooth 630 and more than one input tooth receiving end 640. As will be discussed, the input tooth 630 and the input tooth receiving end 640 of the engagement portion 620 interact with the more than one tooth 440 and more than one tooth receiving end 445 of the outer engagement portion 470 of the tension gear 130 to cause the tension gear 130 to rotate. When the gear locking system 160 is not engaged, actuating of the lever portion 650 causes the engagement portion 620 of the control handle 120 to interact with the outer engagement portion 470 of the tension gear 130 and rotation of the tension gear 130 in a clockwise direction when the lever portion 650 is compressed upwards and rotation of the tension gear 130 in a counterclockwise direction when the lever portion 650 is released.

Figure 7A:
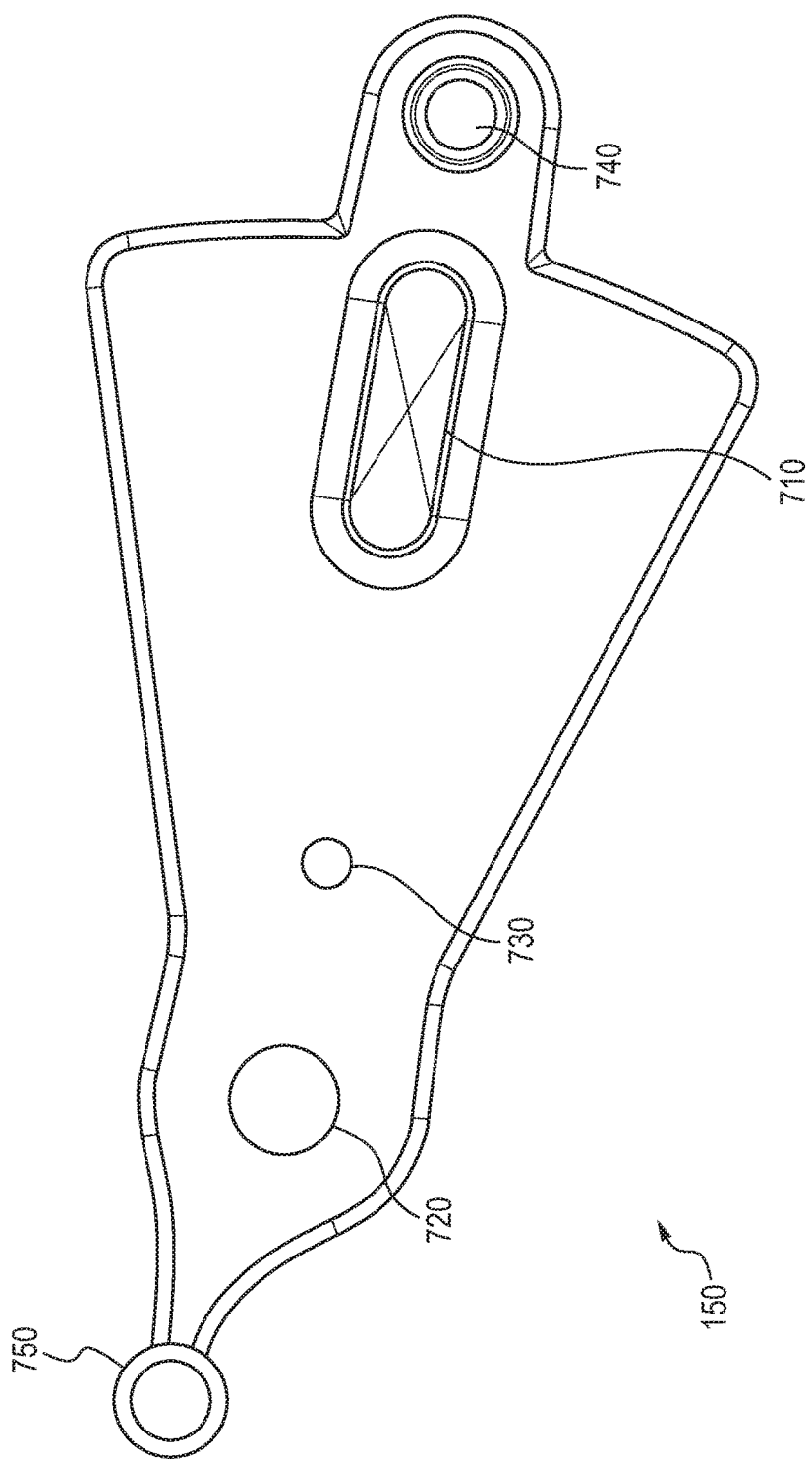
FIG. 7a illustrates a side view of the locking trigger of the deflecting mechanism in FIGS. 2a-b.
Figure 7B:
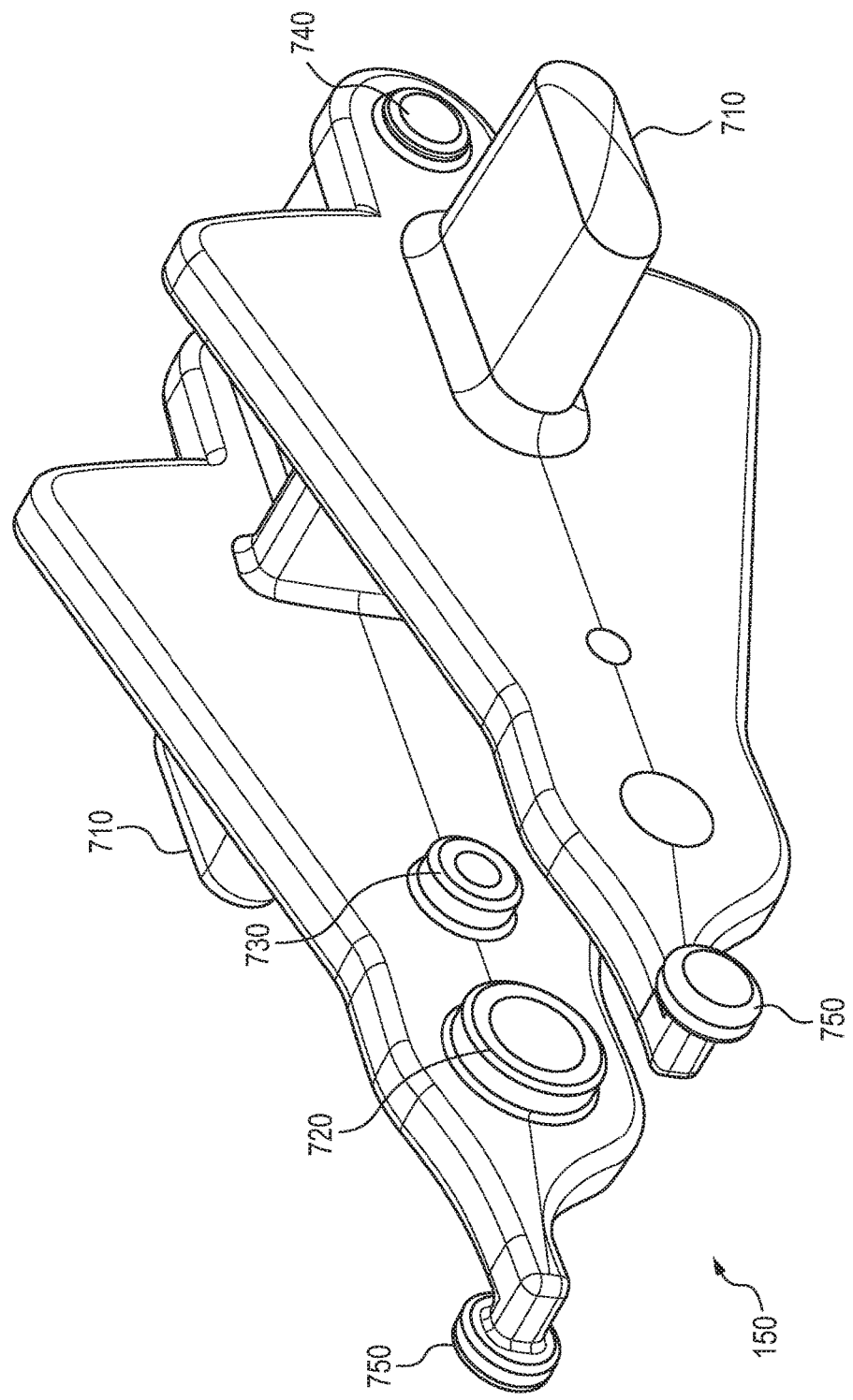
FIG. 7b illustrates a perspective view of the locking trigger of the deflecting mechanism in FIGS. 2a-b.
Figure 8A:
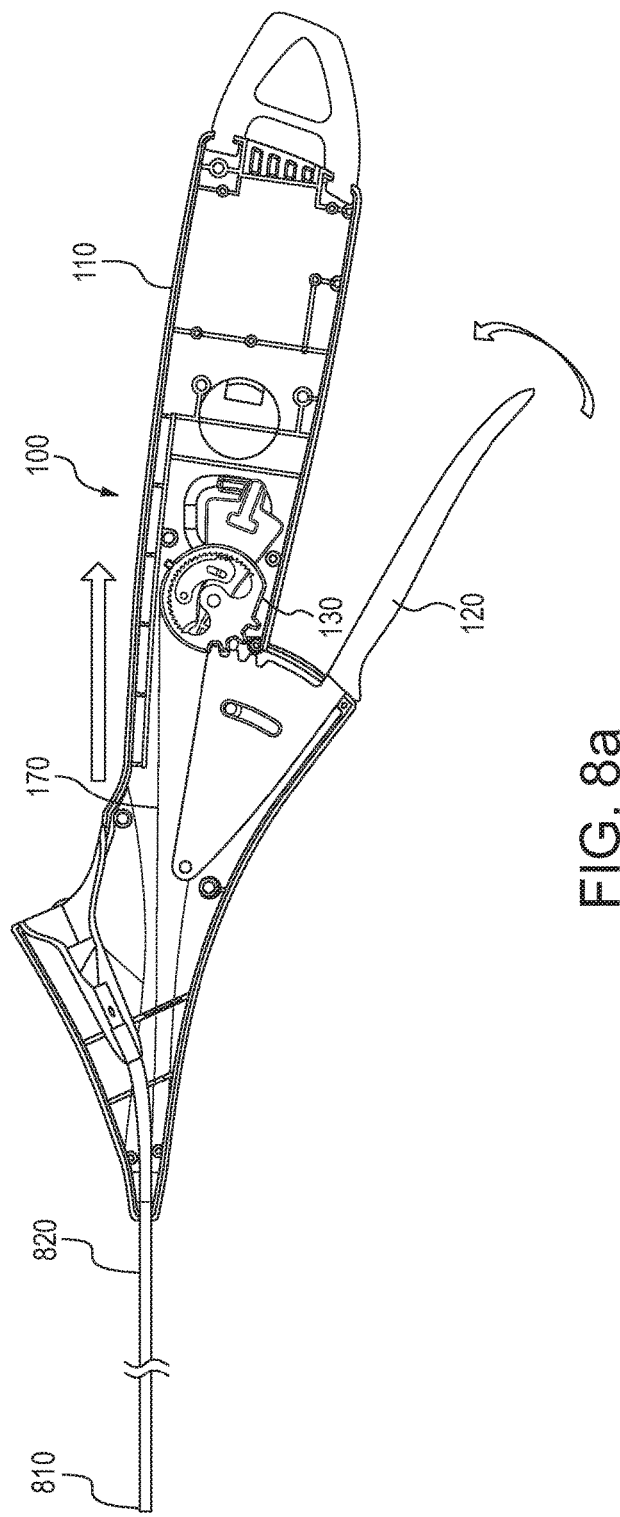
FIG. 8a shows a partial cross-sectional side view of the deflectable access sheath before the deflector filament is retracted in a proximal direction.
Figure 8B:
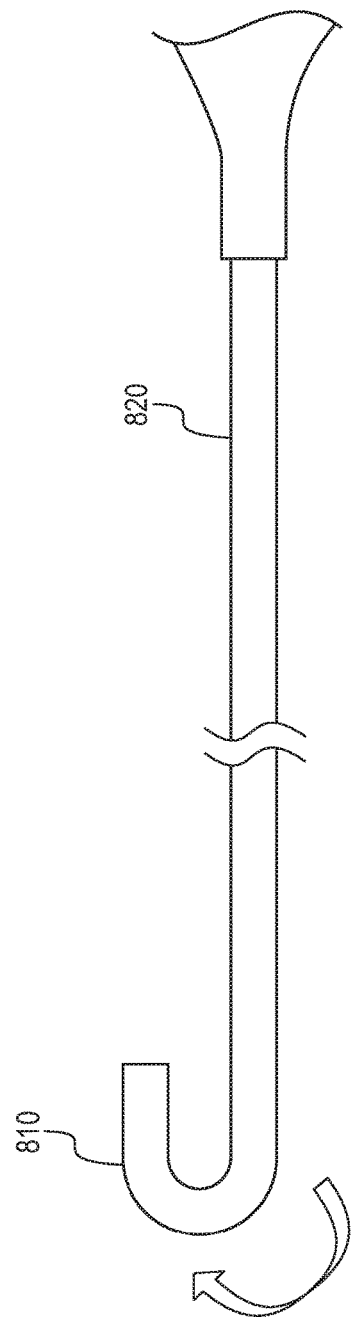
FIG. 8b shows a partial cross-sectional side view of the deflectable access sheath as the deflector filament is retracted in a proximal direction.

FIGS. 7a-7b provide a side and perspective view of the locking trigger 150. In the present embodiment, the locking trigger 150 is composed of elements that control the movement of the locking trigger 150 and elements that actuate the gear locking system 160. The locking trigger 150 has a locking mechanism actuator 710, a tension gear engagement slot 720, a brake pad engagement slot 730, a locking trigger movement pin 740 and a distal pin 750.

The locking trigger 150 is rotatably connected to the sheath housing 110 through the tension gear engagement slot 720 which is disposed about a pin that connects to the slot 330 of the sheath housing 110. The locking trigger 150 is disposed about the tension gear 130 such that the pin that fits into slot 330 of the sheath housing 110 fits through both the tension gear engagement slot 720 and the opening 405 of tension gear 130. The brake pad engagement slot 730 is operatively connected to the brake pad 140 by a pin that extends through the slot portion 530 of the brake pad 140. The pin is connected on either end to the brake pad engagement slot 730 of the locking trigger 150.

The locking mechanism actuator 710 provides the user with control of the movement of the locking trigger 150 and the engagement of the gear locking system 160. The locking mechanism actuator 710 protrudes from the sheath housing 110 at the actuating braking slot 360 to allow the user to actuate the locking mechanism actuator 710 in the actuating braking slot 360. Before the gear locking system 160 is engaged, the pin connected to the brake pad engagement slot 730 is adjacent to the slot top portion 532 of the brake pad 140. The user can engage the gear locking system 160 by actuating the locking mechanism actuator 710 which moves the locking trigger 150 so that the pin connected to the brake pad engagement slot 730 is now adjacent to the slot bottom portion 534 of the brake pad 140. The movement brings the brake pad 140 in contact with the tension gear 130. As discussed above, this engages the gear locking system 160 and creates a ratcheting movement. The brake pad 140 allows movement of the tension gear 130 in a clockwise direction, but prevents the tension gear 130 from moving in a counterclockwise direction. As will be discussed below, when the gear locking system 160 is engaged, subsequent movement in a clockwise direction is limited in increments by the sawtooth 450 on the tension gear 130.

The locking trigger 150 is prevented from moving—whether in its actuated state or non-actuated state—by the locking trigger protrusion 370 of FIG. 3. When the locking mechanism actuator 710 is actuated to engage or disengage the gear locking system 160, the locking trigger movement pin 740 moves above and below either end of the locking trigger protrusion 370 of FIG. 3 which protrudes above the surface of the sheath housing 110. This protrusion prevents the locking trigger movement pin 740 from migrating, and therefore keeps the gear locking system 160 from unintentionally engaging or disengaging.

The distal end of the locking trigger 150 and the distal pin 750 is housed in the locking trigger indicator slot 350 of the sheath housing 110. When the locking mechanism actuator 710 has been actuated to engage the gear locking system 160, the distal pin 750 moves so that it rests in the locking trigger pin indicator 380 of the sheath housing 110. The locking trigger pin indicator 380 is an opening in the sheath housing 110 that allows the distal pin 750 to be visible from outside the sheath housing 110. When the locking mechanism actuator 710 has been actuated to engage the gear locking system 160, the visibility of the distal pin 750 at the locking trigger pin indicator 380 provides the user with a visual cue that the gear locking system 160 has been engaged.

The sheath handle assembly 100 functions to deflect the distal end of the lumen attached to the distal end of the sheath handle assembly 100. FIGS. 8*a*-8*b* illustrate the lumen 820 and the deflectable end 810 as it is deflected away from a linear position. As seen in FIG. 8*a*, the control handle 120 can be compressed to bring it closer to the body of the sheath housing 110. The engagement portion 620 of the control handle 120 interacts with the outer engagement portion 470 of the tension gear 130 to turn the tension gear 130 in a clockwise direction. The proximal end of the tension wire 170 is attached to the filament anchor 430 of the tension gear 130 and the distal end of the tension wire 170 is attached to the lumen 820. As the tension gear 130 moves in a clockwise direction, the tension wire 170 moves in a proximal direction which causes the deflectable end 810 to deflect away from the linear configuration. As seen in FIG. 8*b*, the deflectable end 810 can deflect in a single direction away from the linear configuration. When the control handle 120 is released so that it moves in a direction away from the sheath housing 110, the tension gear 130 moves in a counterclockwise direction. The attached tension wire 170 then moves in a distal direction which causes the deflectable end 810 of the lumen 820 to return to a linear configuration.

The angle of deflection of the deflectable end 810 can be held in place, or adjusted in increments by engaging the gear locking system 160. FIGS. 9-11 illustrate the sheath handle assembly 100 as the gear locking system 160 is engaged.

Figure 9A:
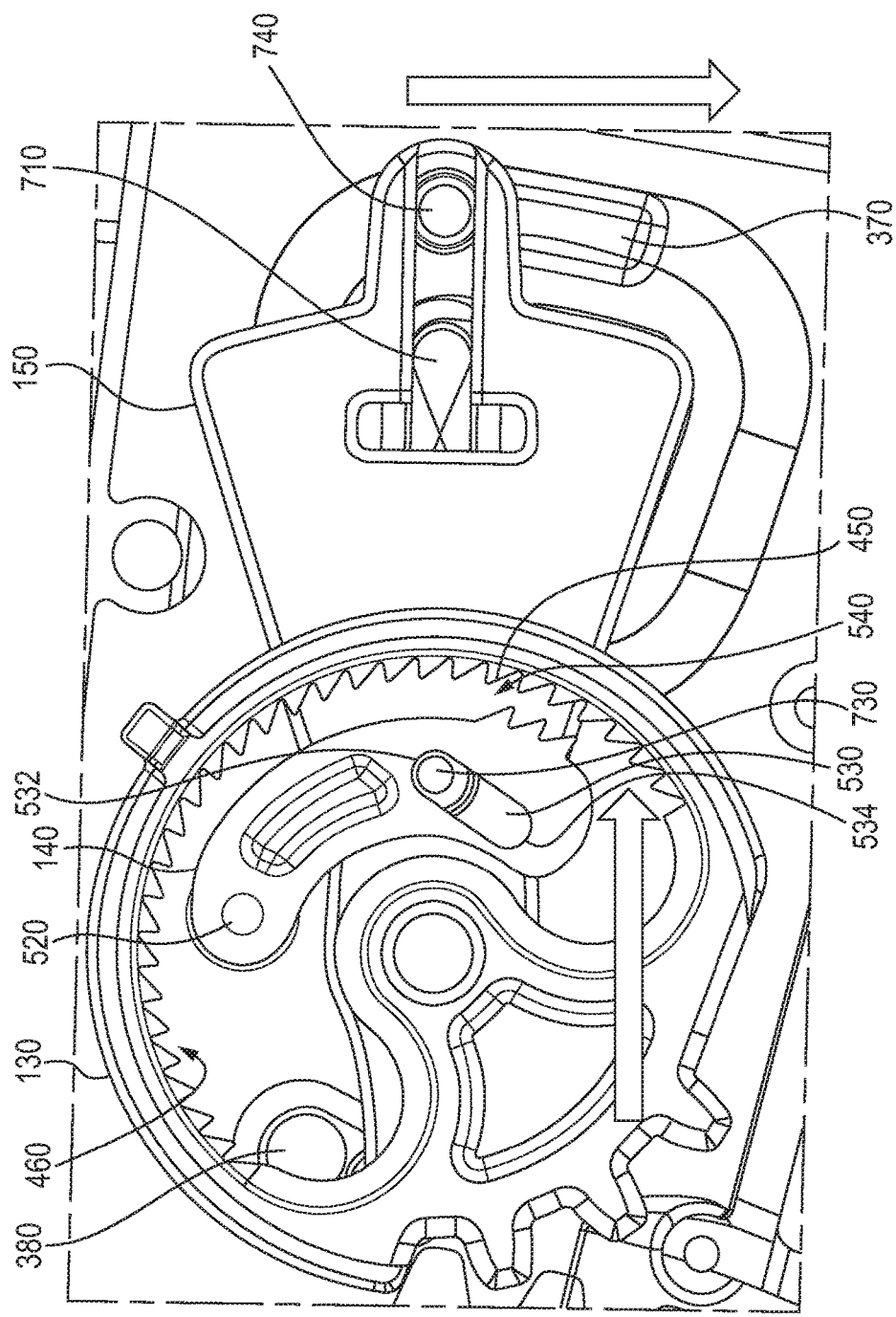
FIG. 9a show the engagement of the locking mechanism before the locking trigger is translated in a downward direction.
Figure 10:
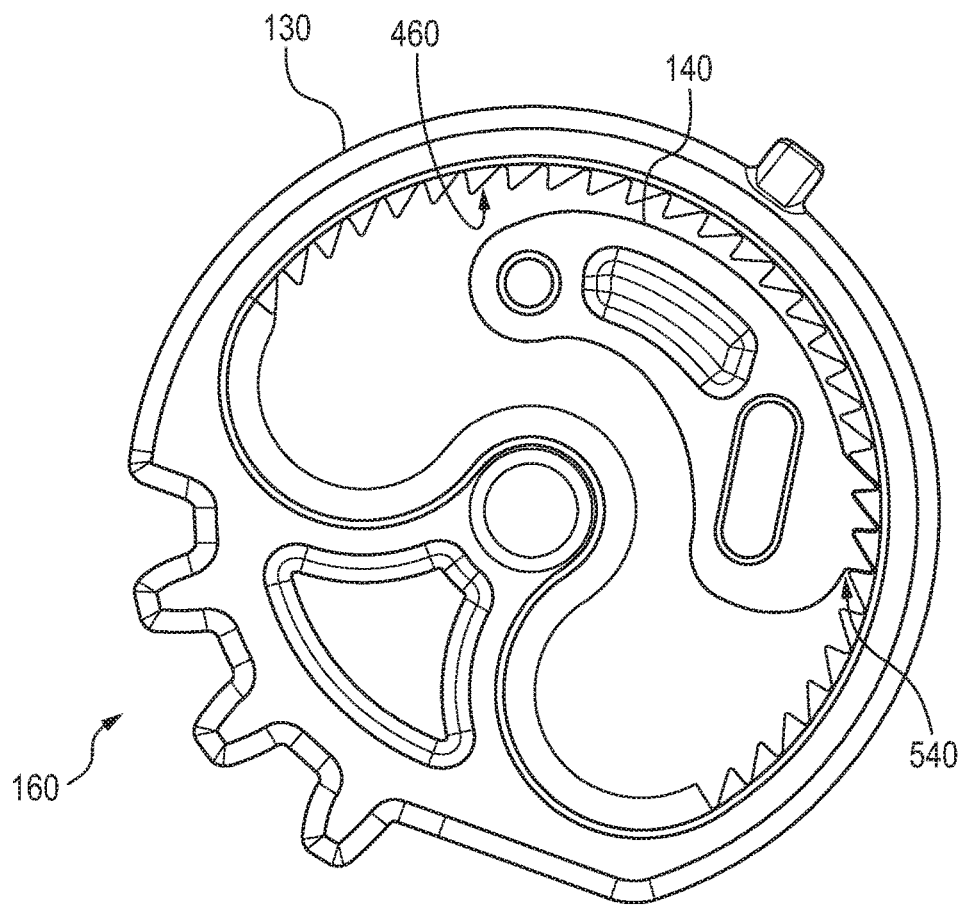
FIG. 10 shows a side view of the locking mechanism as the brake pad engages with the tension gear.

FIG. 9*a* illustrates a cross-section of the sheath handle assembly 100 before the gear locking system 160 is engaged. As can be seen, before the gear locking system 160 is engaged, the pin in the brake pad engagement slot 730 of the locking trigger 150 is located adjacent to the slot top portion 532 of the slot portion 530 of the brake pad 140. In this configuration, the ratchet portion 540 of the brake pad 140 has not engaged the inner engagement portion 460 of the tension gear 130. This allows the control handle 120 to move freely in either direction—to turn the tension gear 130 in a clockwise or a counterclockwise direction (depending on whether the control handle 120 is being compressed or released). This movement slides the tension wire 170 in either a proximal or distal direction to cause the deflectable end 810 of the lumen 820 of FIG. 8*b* to either deflect away from linear or to return to its linear configuration.

Figure 9B:
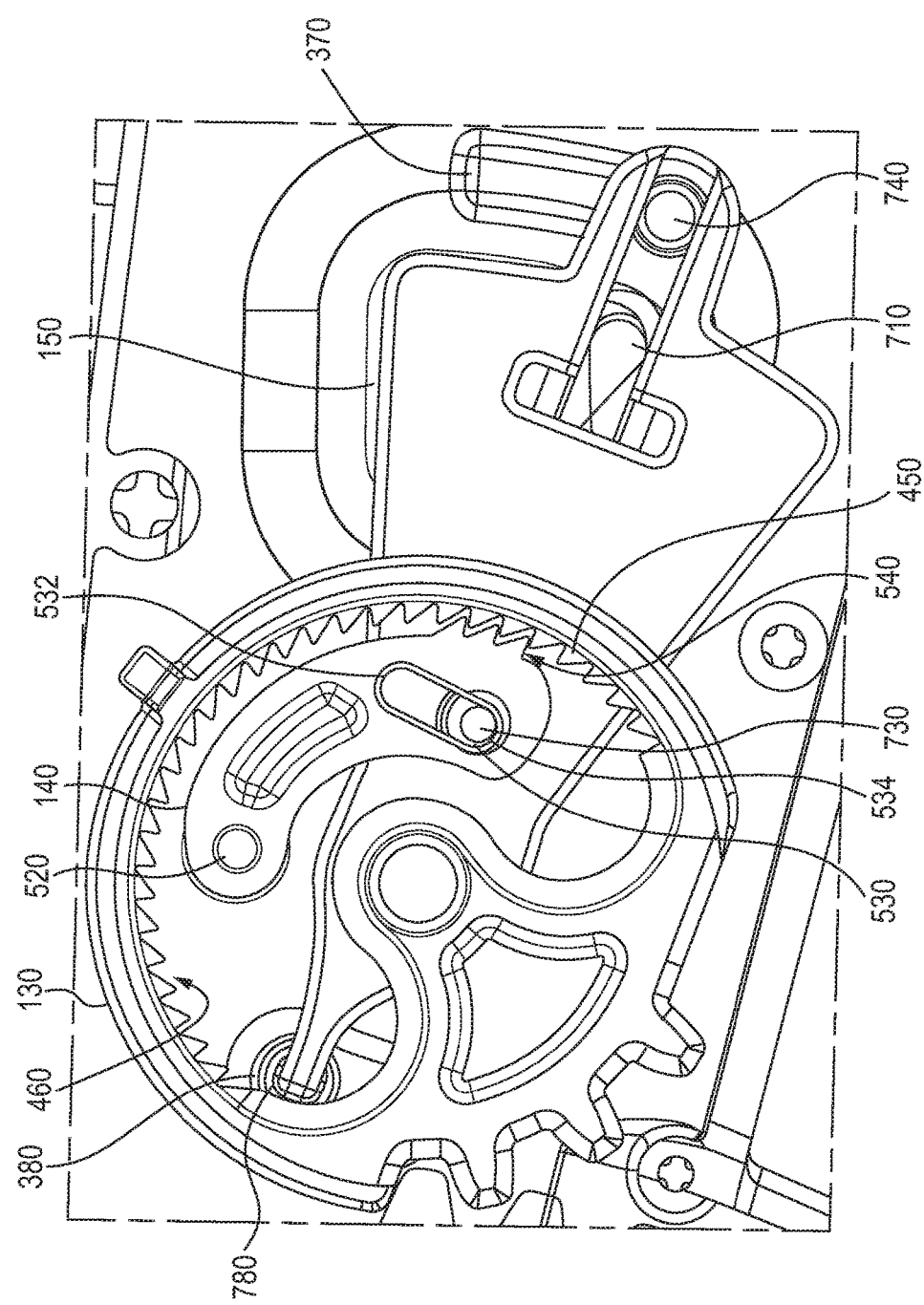
FIG. 9b show the engagement of the locking mechanism after the locking trigger is translated in a downward direction.

FIG. 9*b* illustrates a cross-section of the sheath handle assembly 100 after the gear locking system 160 is engaged. The locking mechanism actuator 710 is actuated in a downward direction. This movement causes the pin in the brake pad engagement slot 730 to move downward so that it lies adjacent to the slot bottom portion 534 of the slot portion 530 of the brake pad 140. This causes the brake pad 140 to rotate about the pin in the opening 520 so that the ratchet portion 540 of the brake pad 140 is brought in contact with the inner engagement portion 460 of the tension gear 130.

The distal pin 750 moves upward so that it comes in contact with the locking trigger pin indicator 380. As mentioned above, this serves as an indicator to the user that the gear locking system 160 is engaged. The distal pin 750 may be colored differently than the sheath housing 110 or have some marking to provide a visual indicator to the user.

The locking trigger movement pin 740 interlocks with the locking trigger protrusion 370 to prevent unintentional movement of the locking trigger 150. The locking trigger protrusion 370 is sloped to allow sliding of the locking trigger movement pin 740 into either configuration. However, without external force, the locking trigger movement pin 740 cannot move into another configuration.

When the gear locking system 160 is engaged, the shape of the teeth on the inner engagement portion 460 of the tension gear 130 and the teeth on the ratchet portion 540 of the brake pad 140 are sloped in a direction that prevent movement of the tension gear 130 in a counterclockwise direction. However, because of the sloped direction of the teeth, the control handle 120 can still be incrementally compressed to allow movement of the tension gear 130 in a clockwise direction. The angle of deflection of the deflectable end 810 can be secured at each increment on the inner engagement portion 460 as represented by each individual sawtooth 450.

When the gear locking system 160 is disengaged, the locking mechanism actuator 710 is actuated in a upward direction which causes the pin in the brake pad engagement slot 730 to move upward so that it lies adjacent to the slot top portion 532 of the slot portion 530 of the brake pad 140. When the gear locking system 160 is disengaged, the angle of deflection of the deflectable end 810 is no longer maintained and the control handle 120 is able to move freely. The tension gear 130 is able to move in both a clockwise and counterclockwise direction to either deflect the deflectable end 810 of the lumen 820 or to return the deflectable end 810 back into a linear configuration.

FIG. 10 provides an enlarged side view of the gear locking system 160 when it is engaged and the ratchet portion 540 of the brake pad 140 is in contact with the inner engagement portion 460 of the tension gear 130.

FIGS. 11*a*-*b* provide a partial side view of the sheath handle assembly 100 before and after the gear locking system 160 has been engaged. FIG. 11*a* shows the locking mechanism actuator 710 of the locking trigger 150 positioned within the actuating braking slot 360 before the gear locking system 160 is engaged. FIG. 11 *b* shows the locking mechanism actuator 710 of the locking trigger 150 within the actuating braking slot 360 after the gear locking system 160 is engaged. FIGS. 11*a*-*b* also show the locking trigger pin indicator 380 which is visible to the user to indicate whether the gear locking system 160 is engaged.

FIGS. 12*a*-*b* provide a side view and a partial bottom view (wherein the friction tension gear 1210 is transparent for better viewing) of an alternate embodiment of the gear locking system 160. The friction gear locking system 1200 of FIGS. 12*a* and *b* is the same as the gear locking system 160 except the friction tension gear 1210 does not have any teeth on the surface of its inner surface 1220 and the friction brake pad 1250 does not have any teeth to engage the friction tension gear 1210 on its outer surface 1260.

The friction tension gear 1210 has all the features of the tension gear 130 except for the inner engagement portion 460 of FIGS. 4*a-b*. The friction tension gear 1210 pictured in FIGS. 12*a-b* has an inner surface 1220 and an outer surface 1230. The inner surface 1220 has a filament receptor 1280 that the tension wire 170 of FIG. 1*b* rests upon. The outer surface 1230 has a chamfered edge 1240 that provides the friction tension gear 1210 with a better grip of the friction brake pad 1250 that it interacts with.

The friction brake pad 1250 has all the features of the tension gear 130 except it lacks the ratchet portion 540 of FIGS. 5*a-b*. The friction brake pad 1250 pictured in FIGS. 12*a-b* has an outer surface 1260 with a friction pad 1270 disposed partially over the outer surface 1260. The friction pad 1270 may be composed of any soft elastomeric material such as rubber, polyisoprene, or thermoelastomers.

The friction gear locking system 1200 has the same function as the gear locking system 160 except that, in place of teeth, when the friction gear locking system 1200 is engaged, the friction pad 1270 of the outer surface 1260 is brought in contact with the chamfered edge 1240 of the inner surface 1220 of the friction tension gear 1210. The friction force between the friction pad 1270 of the friction brake pad 1250 and the chamfered edge 1240 of the friction tension gear 1210 prevents the friction tension gear 1210 from moving in a counterclockwise direction. This embodiment does not have the discrete increments of the gear locking system 160 and therefore does not offer ratcheting. However, it provides for greater flexibility in controlling the deflectable end 810 of the lumen 820.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:

1. An elongate access sheath, comprising:
a distal portion, a proximal portion, and an elongate portion extending between the proximal portion and the distal portion, wherein the elongate portion defines a lumen, and the distal portion is bendable with respect to a longitudinal axis of the elongate portion;
the proximal portion supporting a control handle, a brake pad, a locking trigger, and a tension gear;
a deflector filament slidably extending through the lumen, and operatively coupled to said distal portion and said tension gear, wherein said deflector filament is mounted such that rotation of said tension gear urges sliding movement within said lumen;
wherein said tension gear is rotatably mounted to the proximal portion and includes an outside engagement portion, wherein said outside engagement portion comprises teeth that are located on the outside engagement portion of said tension gear;
wherein said control handle comprising a lever portion and an engagement portion that comprises input teeth, wherein the input teeth of the engagement portion are meshed with the outside engagement portion of said tension gear such that upward movement of the lever portion causes rotation of said tension gear in a first direction and sliding motion of the deflector filament within the lumen to urge the distal portion to bend with respect to the longitudinal axis;
wherein said brake pad is disposed within a hollow center of said tension gear and comprises a slot and an outside engagement portion, wherein said slot is disposed vertically on said brake pad and said outside engagement portion of the brake pad is aligned to engage an inner engagement portion of said tension gear;
wherein said locking trigger is attached to said tension gear and includes a body portion and a pin, wherein said pin is disposed within the slot of said brake pad; and
wherein the locking trigger is configured to translate to cause the pin to slide within the slot and urge engagement between the brake pad and said tension gear thereby preventing rotation of said tension gear in an opposite second direction.

2. The elongate access sheath of claim 1 wherein said locking trigger can be translated to cause said pin of said locking trigger to slide in said slot of said brake pad to allow rotation of said tension gear in said opposite second direction.

3. The elongate access sheath of claim 1 wherein said locking trigger protrudes from said elongate access sheath to allow actuation of said locking trigger.

4. The elongate access sheath of claim 1 wherein said proximal portion of said elongate access sheath includes an indicator that is actuated when said locking trigger is translated to engage the brake pad and said tension gear.

5. An elongate access sheath, comprising:
a distal portion, a proximal portion, and an elongate portion extending between the proximal portion and the distal portion, wherein the elongate portion defines a lumen, and the distal portion is bendable with respect to a longitudinal axis of the elongate portion;
the proximal portion supporting a control handle, a brake pad, a tension gear, and a locking trigger;
a deflector filament slidably extending through the lumen, and operatively coupled to said distal portion and said tension gear, wherein said deflector filament is mounted such that rotation of said tension gear urges sliding movement within said lumen;
wherein said tension gear is rotatably mounted to the proximal portion and includes an outside engagement portion and an inner engagement portion defined within a hollow center of said tension gear, wherein said outside engagement portion comprises teeth;
wherein said brake pad is disposed within said hollow center of said tension gear and comprises a slot and a ratchet portion disposed upon an outer surface of the brake pad, wherein said slot is disposed vertically on said brake pad, wherein the ratchet portion is aligned to engage the inner engagement portion of said tension gear;
said locking trigger is attached to said tension gear and includes a body portion and a pin, wherein said pin is disposed within the slot of said brake pad;
said control handle comprising a lever portion and an engagement portion that comprises input teeth, wherein the input teeth of the engagement portion are meshed with the outside engagement portion of said tension gear such that upward movement of the lever portion causes rotation of said tension gear in a first direction and sliding motion of the deflector filament within the lumen to urge the distal portion to bend with respect to the longitudinal axis, wherein the locking trigger is configured to translate to cause the pin to slide within the slot and urge engagement between said ratchet portion of the brake pad and said inner engagement portion of the tension gear thereby preventing rotation of said tension gear in an opposite second direction.

6. The elongate access sheath of claim 5 wherein said ratchet portion is comprised of angled teeth, wherein said angled teeth are angled in the opposite second direction to restrict movement of said tension gear when said brake pad and said tension gear are engaged; and wherein said ratchet portion allows further rotation of said tension gear in the first direction upon additional upward movement of said lever portion while preventing rotation of said tension gear in an opposite second direction.

7. The elongate access sheath of claim 5 wherein said locking trigger can be translated to cause said pin of said locking trigger to slide in said slot of said brake pad to allow rotation of said tension gear in said opposite second direction.

8. The elongate access sheath of claim 5 wherein said locking trigger protrudes from said elongate access sheath to allow actuation of said locking trigger.

9. The elongate access sheath of claim 5 wherein said proximal portion of said elongate access sheath includes an indicator that is actuated when said locking trigger is translated to engage the brake pad and said tension gear.

10. An elongate access sheath, comprising:
a distal portion, a proximal portion, and an elongate portion extending between the proximal portion and the distal portion, wherein the elongate portion defines a lumen, and the distal portion is bendable with respect to a longitudinal axis of the elongate portion;
the proximal portion supporting a control handle, a brake pad, a tension gear, and a locking trigger;
a deflector filament slidably extending through the lumen, and operatively coupled to said distal portion and said tension gear, wherein said deflector filament is mounted such that rotation of said tension gear urges sliding movement within said lumen;
wherein said tension gear is rotatably mounted to the proximal portion and includes an outside engagement portion and an inner engagement portion, wherein said outside engagement portion comprises teeth that are located on an outer surface of said tension gear;
wherein said brake pad is disposed within a hollow center of said tension gear and comprises a slot and a friction portion, wherein said slot is disposed vertically on said brake pad and said friction portion is located on an outer surface of said brake pad and aligned to engage the inner engagement portion of said tension gear;
said locking trigger is attached to said tension gear and includes a body portion and a pin, wherein said pin is disposed within the slot of said brake pad;
said control handle comprising a lever portion and an engagement portion that comprises input teeth, wherein the input teeth of the engagement portion are meshed with the outside engagement portion of said tension gear such that upward movement of the lever portion causes rotation of said tension gear in a first direction and sliding motion of the deflector filament within the lumen to urge the distal portion to bend with respect to the longitudinal axis, wherein the locking trigger is configured to translate to cause the pin to slide within the slot and urge engagement between the brake pad and said tension gear thereby preventing rotation of the tension gear in an opposite second direction.

11. The elongate access sheath of claim 10 wherein said inner engagement portion of said tension gear has a chamfered edge.

12. The elongate access sheath of claim 10 wherein said locking trigger can be translated to cause said pin of said locking trigger to slide in said slot of said brake pad to allow rotation of said tension gear in said opposite second direction.

13. The elongate access sheath of claim 10 wherein said locking trigger protrudes from said elongate access sheath to allow actuation of said locking trigger.

14. The elongate access sheath of claim 10 wherein said proximal portion of said elongate access sheath includes an indicator that is actuated when said locking trigger is translated to engage the brake pad and said tension gear.

* * * * *